United States Patent
Cassidy et al.

(10) Patent No.: US 6,280,474 B1
(45) Date of Patent: *Aug. 28, 2001

(54) DEVICES FOR TISSUE REPAIR AND METHODS FOR PREPARATION AND USE THEREOF

(75) Inventors: James J. Cassidy, Shakopee, MN (US); Jeff E. Yeung, San Jose, CA (US); Jacqueline Anne Schroeder, Redwood City, CA (US); Vivek Shenoy, Sunnyvale, CA (US); Melissa K. C. Brown, Los Altos, CA (US)

(73) Assignee: Neucoll, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/362,124

(22) Filed: Jul. 27, 1999

Related U.S. Application Data

(60) Division of application No. 09/004,550, filed on Jan. 8, 1998, now Pat. No. 6,083,522, which is a continuation-in-part of application No. 08/833,874, filed on Apr. 10, 1997, now abandoned, which is a continuation-in-part of application No. 08/781,012, filed on Jan. 9, 1997, now abandoned.

(51) Int. Cl.$^7$ ........................................... A61F 2/16

(52) U.S. Cl. ........................................ 623/16.11; 606/232

(58) Field of Search ...................... 623/11, 12, 15, 623/16, 18, 23.58, 16.11, 13.14; 424/423; 606/232, 73–77

(56) References Cited

U.S. PATENT DOCUMENTS

| | | |
|---|---|---|
| 3,187,383 | 6/1965 | Bacchus et al. . |
| 4,140,537 | 2/1979 | Luck et al. . |
| 4,164,559 | 8/1979 | Miyata et al. . |

(List continued on next page.)

FOREIGN PATENT DOCUMENTS

| | | |
|---|---|---|
| 0 412 280 | 2/1991 | (EP) . |
| 0 668 081 | 8/1995 | (EP) . |
| 0 700 671 A1 | 3/1996 | (EP) . |
| 0 713 707 A1 | 5/1996 | (EP) . |
| 2 131 293 | 6/1984 | (GB) . |
| 2 167 514 | 5/1986 | (GB) . |
| WO 89/11301 | 11/1989 | (WO) . |
| WO 94/01483 | 1/1994 | (WO) . |
| WO 94/16570 | 8/1994 | (WO) . |
| WO 96/14095 | 5/1996 | (WO) . |
| WO 96/39169 | 12/1996 | (WO) . |
| WO 97/22372 | 6/1997 | (WO) . |

OTHER PUBLICATIONS

Barber, F.A. "Strength of Sutures and Suture Anchors: Update 1996." *AAOS Specialty Day*.(1996).

Barber, F.A. "Suture Anchor Failure Strength—An In Vivo Study." *Arthroscopy*.(1993)9(6):647–652.

Barber, F.A. "The Ultimate Strength of Suture Anchors." *Arthroscopy*.(1995)11(1):21–28.

Burkhart, S.S. "The Deadman Theory of Suture Anchors: Observations Along a South Texas Fence Line." *Arthroscopy*.(1995)11(1):119–123.

Carpenter, J.E. et al., "Pull–out Strength of Five Suture Anchors." *Arthroscopy*.(1993)9(1):109–113.

Claes, L.E. et al., "New Bioresorbable pin for the Reduction of Small Bony Fragments: Design, Mechanical Properties and In Vitro Degradation."*Biomaterials*.(1996)17(6):1621–25.

(List continued on next page.)

*Primary Examiner*—Henry J. Recla
*Assistant Examiner*—(Jackie) Tan-Uyen T. Ho
(74) *Attorney, Agent, or Firm*—Morrison & Foerster LLP

(57) ABSTRACT

Methods and implant devices for use in tissue repair. The implant devices include resorbable, swellable implant bodies, formed from a dehydrated crosslinked biocompatible polymer. The implant devices are capable of swelling after insertion into tissues to become anchored in place.

13 Claims, 23 Drawing Sheets

U.S. PATENT DOCUMENTS

| | | |
|---|---|---|
| 4,410,537 | 10/1983 | Kneen . |
| 4,424,208 | 1/1984 | Wallace et al. . |
| 4,488,911 | 12/1984 | Luck et al. . |
| 4,533,358 | 8/1985 | Yoden et al. . |
| 4,544,516 | 10/1985 | Hughes et al. . |
| 4,563,350 | 1/1986 | Nathan et al. . |
| 4,582,640 | 4/1986 | Smestad et al. . |
| 4,642,117 * | 2/1987 | Nguyen et al. ................... 623/11 |
| 4,743,229 | 5/1988 | Chu . |
| 4,776,890 | 10/1988 | Chu . |
| 4,795,467 | 1/1989 | Piez et al. . |
| 4,803,075 | 2/1989 | Wallace et al. . |
| 4,888,366 | 12/1989 | Chu et al. . |
| 4,923,380 | 5/1990 | Huc et al. . |
| 4,947,840 * | 8/1990 | Yannas et al. ................... 623/15 |
| 5,035,715 | 7/1991 | Smestad et al. . |
| 5,110,604 | 5/1992 | Chu et al. . |
| 5,162,430 | 11/1992 | Rhee et al. . |
| 5,226,877 | 7/1993 | Epstein . |
| 5,290,552 | 3/1994 | Sierra et al. . |
| 5,294,249 | 3/1994 | Luisi . |
| 5,304,595 | 4/1994 | Rhee et al. . |
| 5,306,500 | 4/1994 | Rhee et al. . |
| 5,322,648 | 6/1994 | Dapper . |
| 5,324,775 | 6/1994 | Rhee et al. . |
| 5,328,955 | 7/1994 | Rhee et al. . |
| 5,376,375 | 12/1994 | Rhee et al. . |
| 5,413,791 | 5/1995 | Rhee et al. . |
| 5,428,022 | 6/1995 | Palefsky et al. . |
| 5,446,091 | 8/1995 | Rhee et al. . |
| 5,475,052 | 12/1995 | Rhee et al. . |
| 5,478,342 * | 12/1995 | Kohrs ................................ 606/73 |
| 5,489,210 * | 2/1996 | Hanosh ........................... 433/173 |
| 5,501,706 | 3/1996 | Arenberg . |
| 5,523,348 | 6/1996 | Rhee et al. . |
| 5,527,856 * | 6/1996 | Rhee et al. ..................... 525/54.1 |
| 5,550,187 * | 8/1996 | Rhee et al. ..................... 525/54.1 |
| 5,580,923 | 12/1996 | Yeung et al. . |
| 5,643,464 * | 7/1997 | Rhee et al. ...................... 210/748 |
| 5,709,687 * | 1/1998 | Pennig ............................. 606/73 |
| 5,709,934 * | 1/1998 | Bell et al. ......................... 623/15 |
| 5,718,717 | 2/1998 | Bonutti . |
| 5,735,902 * | 4/1998 | Li et al. ........................... 623/18 |
| 5,800,541 * | 9/1998 | Rhee et al. ....................... 623/11 |
| 5,837,752 * | 11/1998 | Shastri et al. ................... 523/116 |
| 5,919,193 * | 7/1999 | Slavitt ............................. 606/72 |
| 6,110,482 * | 8/2000 | Khouri et al. .................... 623/16 |

OTHER PUBLICATIONS

Cornell, C.N. et al. (1991). "Multicenter trial of Collagraft as bone graft substitute," *J. Orthop. Trauma.* 5(1):1–8.

Firoozbakhsh, K.K. et al., "Staple Leg Profile Influence on Pullout Strength." *Clinical Orth. and Related Research*.(1996)No. 331:300–307.

France, E.P. et al., "Biomechanical Evaluation of Rotator Cuff Fixation Methods." *Am. J. of Sports Med*.(1989)17(2):176–181.

Gerber, C. et al., "Mechanical Strength of Repairs of the Rotator Cuff." *J. of Bone and Joint Surgery*. (1994)37B(3):371–80.

Glowacki, K.A. et al., "Distal Radius Fractures: Concepts and Complications." *Orthopedics*.(1996)19(7):601–607.

Guyton, A.C. *Textbook of Medical Physiology*. 3rd Ed. Philadelphia: W.B. Saunders Co., 1966. vii–xxxiii (Table of Contents).

Hecker, A.T. et al., "Pull–out Strengh of Suture Anchors for Rotator Cuff and Bankart Lesion Repairs." *Am. J. of Sports Med.* (1993)21(6):874–79.

Jakob, H. et al. (1984). "Combined application of heterologous collagen and fibrin sealant for liver injuries," *J. Surg. Res.* 36:571–577.

Kalmar, P. et al. (1982). "Bioadhesives in cardiac and vascular surgery," *Thorac. Cardiovasc. Surg.* 30:230–231.

Keefe, J. et al. (1992). "Clinical use of injectable bovine collagen: A decade of experience," *Clin. Mater.* 9:155–162.

Kennedy, J.G. et al. (May 1984). "Use of cryoprecipitate coagulum to control tumor–bed bleeding," *J. Neurosurg.* 60:1099–1101.

Koveker, G. (1982). "Clincal application of fibrin glue in cardiovascular surgery," *Thorac. Cardiovasc. Surg.* 30:228–229.

Lagoutte, F.M. (1989). "A fibrin sealant for perofrated and preperforated corneal ulcers," *Br. J. Ophthal.* 73:757–761.

Meisner, H. et al. (1982). "Fibrin seal application. Clinical experience," *Thorac. Cardiovasc. Surg.* 30:232–233.

Mori, S. (Jul. 1985). "Spontaneous posterior bulbar perforation of congenital scleral coloboma and its surgical treatment: A case report," *Ophtal. Surg.* 16(7):433–436.

Pagnani, M.J. (1995). "Arthroscopic fixation of superior labral lesions using a biodegradable implant: a preliminary report," *Arthroscopy* 11(2):194–198.

Pagnani, M.J. et al., "Arthroscopic Shoulder Stabilization." *Operative Tech. in Sports Med.*.(1993)1(4):276–284.

Paulos, L.E. et al., "Augmentation of Rotator Cuff Repair: In Vivo Evaluation in Primates." *Orthopedic Research Society*.Feb. 5–8 (1990).

Piechotta, F.–U. et al. (1983). "The maximization of wound healing with fibrin glue," *Aesth. Plast. Surg.* 7:81–82.

Reed, S.C. et al., "Full–Thickness Rotator Cuff Tears." *Am. J. of Sports Med.* (1996)24(1):46–48.

Rostron, C.K. (Aug. 1988). "Experimental epikeratophakia with biological adhesive," *Arch. Ophthalmol.* 106:1103–1106.

Rousou, J. et al. (1989). "Randomized clinical trialof fibrin sealant in patients undergoing resternotomy or reoperation after cardiac operations," *J. Thorac. Cardiovasc. Surg.* 97:194–203.

Rousou, J.A. et al. (Oct. 1984). "Fibrin glue: An effective hemostatic agent for nonsuturable intraoperative bleeding," *Ann. Thorac. Surg.* 38(4):409–410.

Shall, L.M. et al., "Soft Tissue Reconstruction in the Shoulder." *Am. J. of Sports Med.*, (1994)22(5):715–18.

Sherer Jr., J.F. (May 1980). "Cryoprecipitate coagulum pyelolithotomy," *J. Urol.* 123:621–624.

Stark, J. et al. (Oct. 1984). "Experience with fibrin seal (Tisseel) in operations for congenital heart defects," *Ann. Thorac. Surg.* 38(4):411–413.

Tamai, K. et al., "Efficacy and Pitfalls of the STATAK Soft–tissue Attachment Device for the Bankart Repair." *J. Shoulder Elbow Surg*.(1993)2(4):216–20.

Victoroff, B.N. et al., "Arthroscopic Bone Peg Fixation in the Treatment of Osteochondritis Dissecans in the Knee." *Arthroscopy*.(1996)12(4):506–509.

Walsh, W.R. et al., "Biomechanical Evaluation of Bankart Reconstructions in a Human Cadaver Shoulder Model." *Fifth World Biomaterials Congress*. May 29–Jun. 2 (1996).

Wallace, D.G. et al. (1992). "Tissue compatability of collagen–silicone composites in a rat subcutaneous model," *J. Biomed. Mat. Res.* 26:1517–1534.

Warner, J.P. et al., "Arthroscopic Bankart Repair With the Suretac Device. Part I: Clinical Observations." *Arthroscopy*.(1995)11(1):2–13.

Warner, J.P. et al., "Arthroscopic Bankart Repair With the Suretac Device. Part II: Experimental Observations." *Arthroscopy*.(1995)11(1):14–20.

Warner, J.P. et al., "Arthroscopic Repair of Combined Bankart and Superior Labral Detachment Anterior and Posterior Lesions: Technique and Preliminary Results." *Arthroscopy*.(1994)10(4):383–391.

Weiler, A. et al., "Foreign–body Reaction and the Course of Osteolysis After Polyglycolide Implants for Fracture Fixation." *J. of Bone and Joint Surgery*.(1996)78B(3):369–375.

Williams, H.L. *Polymer Engineering*. New York: Elsevier, 1975. vii (Table of Contents).

Zilch, H. et al. (1986). "The sustained release of cefotaxim from a fibrin–cefotaxim compound in treatment of osteitis," *Arch. Orthop. Trauma. Surg.* 106:36–41.

* cited by examiner

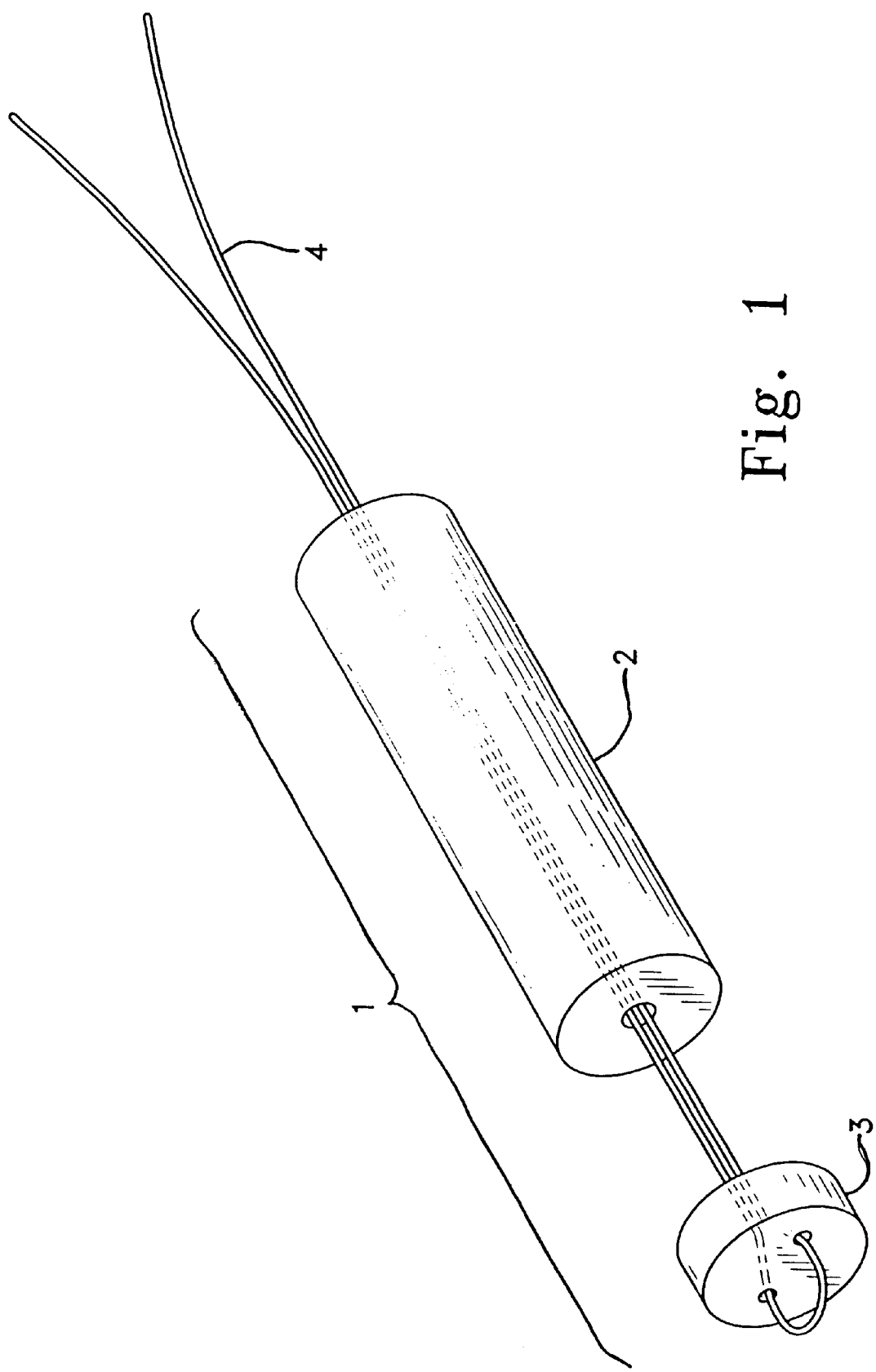

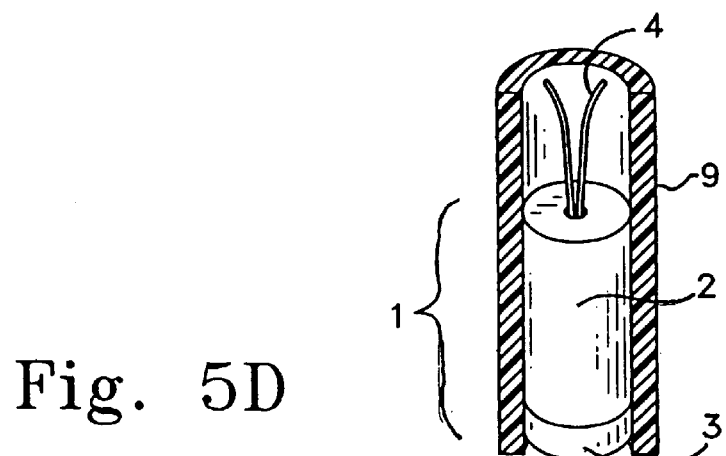
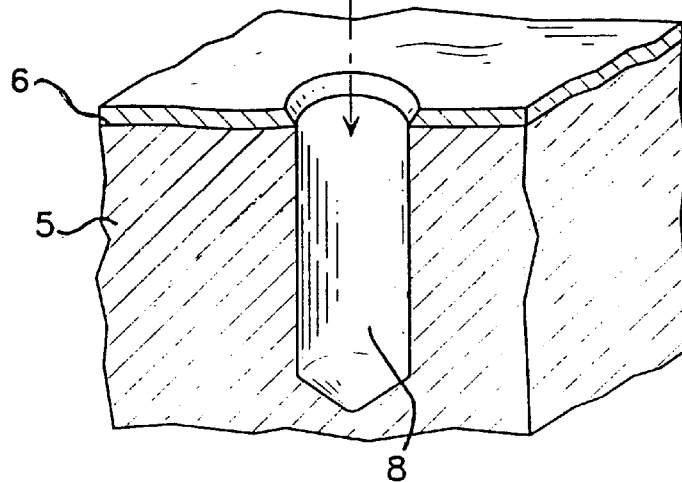
Fig. 5D
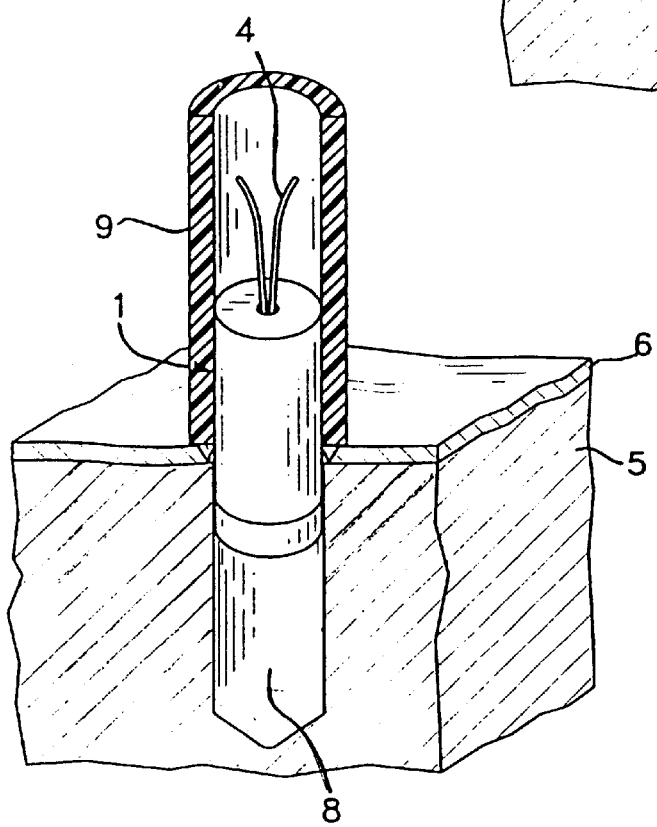
Fig. 5E

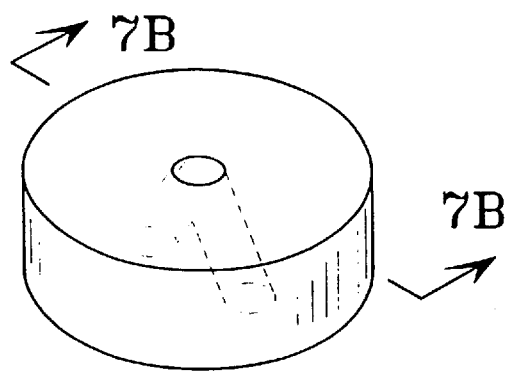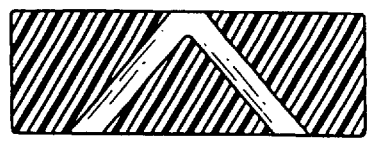
Fig. 7A  Fig. 7B
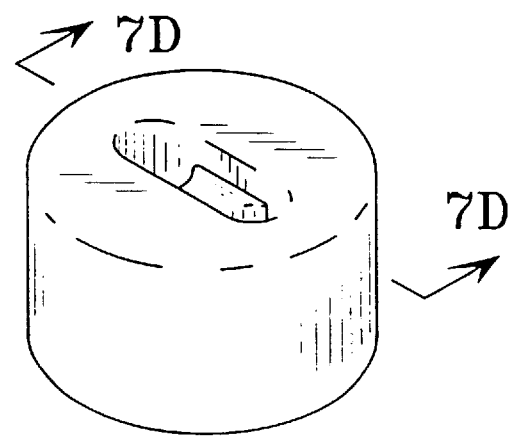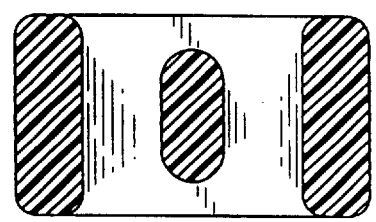
Fig. 7C  Fig. 7D
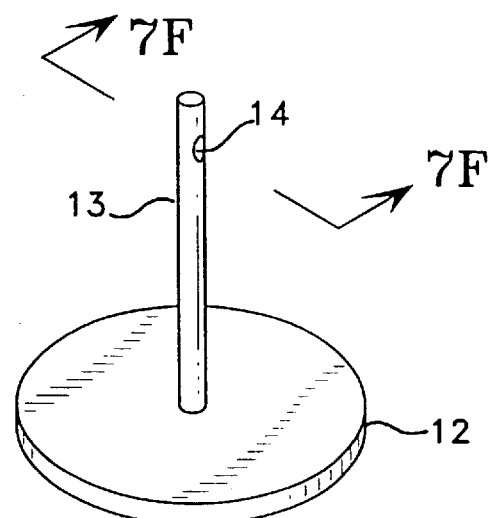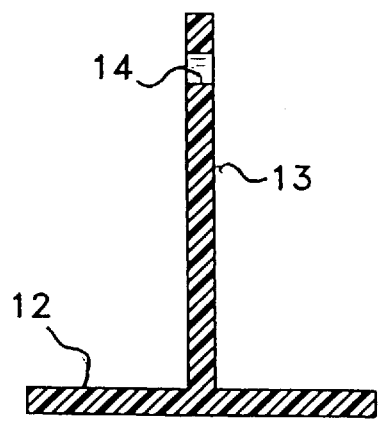
Fig. 7E  Fig. 7F

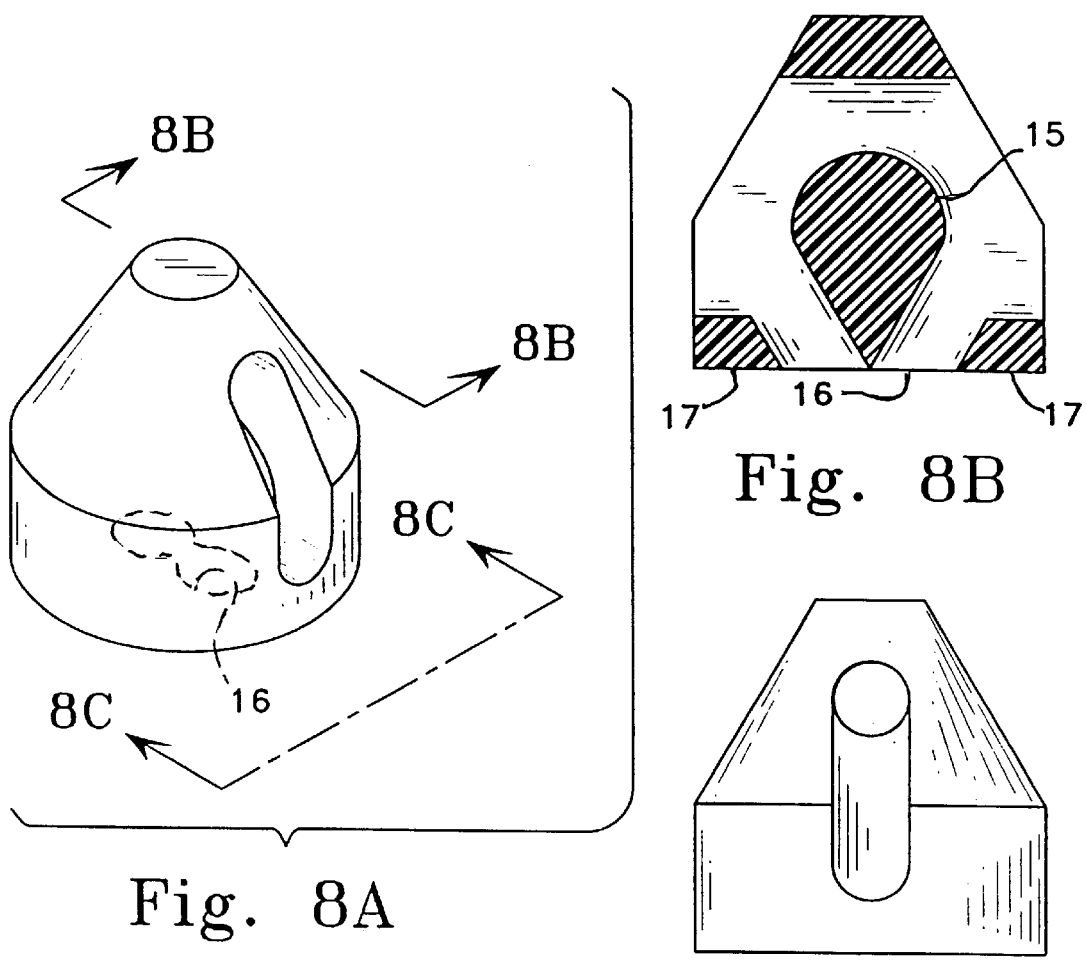
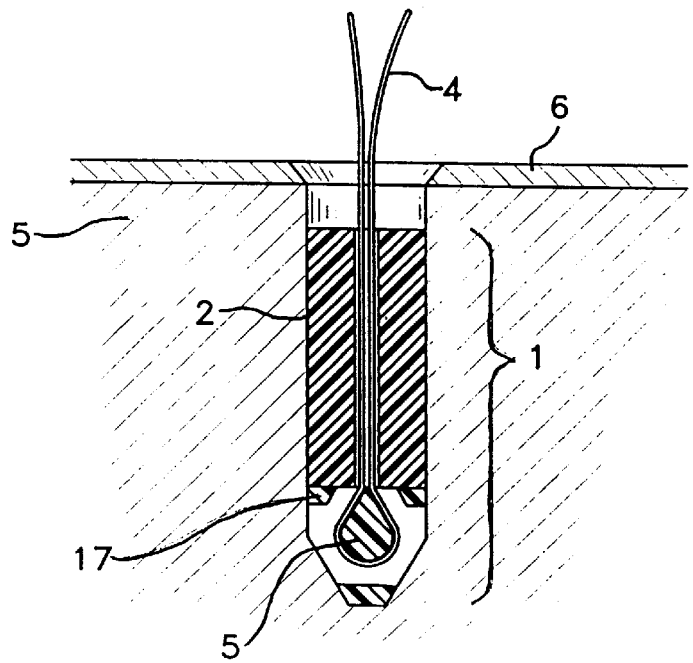
Fig. 8A
Fig. 8B
Fig. 8C
Fig. 8D

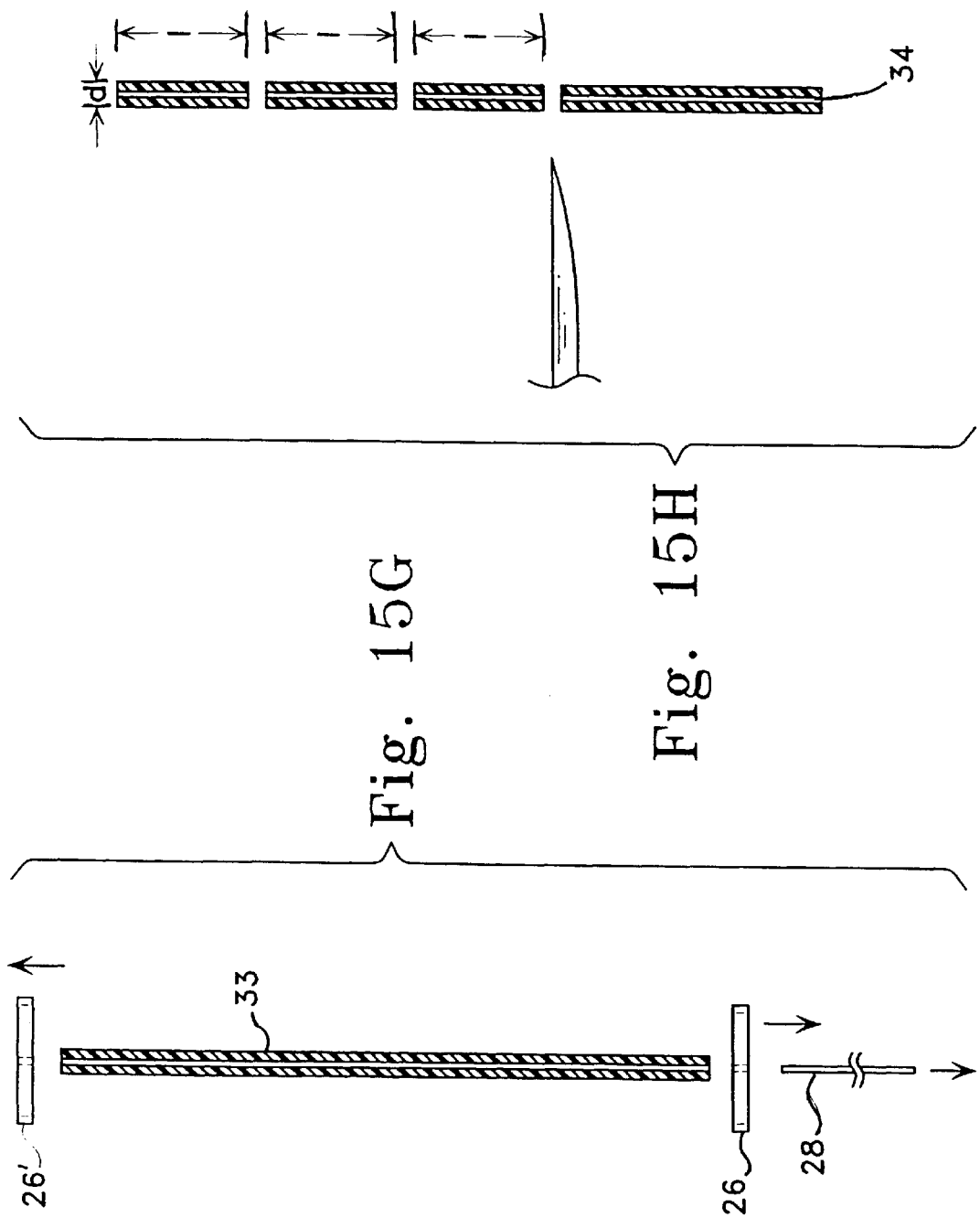

DEVICES FOR TISSUE REPAIR AND METHODS FOR PREPARATION AND USE THEREOF

CROSS-REFERENCE TO RELATED APPLICATIONS

This application is a divisional of U.S. application Ser. No. 09/004,550, filed Jan. 8, 1998, which is a continuation-in-part of U.S. application Ser. No. 08/833,874, filed on Apr. 10, 1997, now abandoned which is a continuation-in-part of U.S. application Ser. No. 08/781,012, filed on Jan. 9, 1997, now abandoned, each of which is incorporated herein in its entirety.

FIELD OF THE INVENTION

This invention relates to uniformly shaped swellable devices comprising polymeric materials. This invention also provides methods and apparatuses for making such swellable devices. In a preferred embodiment, this invention provides for implants for use in tissue repair comprising dehydrated biocompatible crosslinked polymeric matrices and methods and apparatuses for their manufacture and use.

BACKGROUND OF THE INVENTION

Uniformly shaped devices which are capable of swelling when exposed to an aqueous environment have applications in a wide variety of different fields where there is a need to provide temporary or permanent filling or blocking of a lumen, space or void. For example, such devices may be useful in oceanography or plumbing. However, these types of devices are particularly useful for in vivo applications where the shapes of implantable devices and their properties when exposed to in vivo conditions are important. For example, in the field of orthopedics, uniformly shaped devices are useful for implantation into surgically preformed or naturally occurring voids in hard tissue for facilitating bone repair.

Bone repair is necessary to treat a variety of orthopedic conditions. For example, when hard tissue such as bone is damaged as a result of disease or injury, it is often necessary to provide a means for strengthening the damaged bone during the healing process to prevent further damage. This can be achieved externally by placing the area of the body in which the damaged bone is located in a supporting device such as a cast. Alternatively, in the more severe situations where direct support is necessary, the damaged bone can be supported by implanting surgical devices such as metal pins and rods to which the damaged bone is attached while healing.

In many instances, when the bone is severely damaged, or when the damaged tissue necessitates more immediate treatment (i.e. when it is not feasible to wait for the natural healing process to occur), it becomes necessary to increase the integrity and thus the load bearing capacity of the bone itself by using implants that are placed within the tissue. Such implants may take the form of plugs or rods, which are placed in the hard tissue after forming a depression or channel therein.

In other instances, tissue damage results in the dissociation of two or more tissues, most often a soft tissue such as tendon or ligament which detaches from bone. In such situations, it is necessary to reattach the tissues together either permanently, or temporarily while the two tissues became permanently reattached during the healing process. Devices for reattaching tissues have been described in the literature. For example, Innovasive Devices, Inc. (Marlborough, Mass.) markets a device called the ROC™ Fastener which is a nonresorbable, permanent synthetic insert. Other synthetic devices include the following: metal barbed anchors which are designed to hold a suture (Mitek, Norwood, Mass.); metal screws to which suture material can be attached (Linvatec, Largo, Fla.); and plastic suture anchors with expandable wings (Acufex Microsurgical, Inc., Norwood, Mass.).

Unlike the synthetic permanent implants heretofore described, some manufacturers have recently described the use of hydrolizable inserts. For example, the Suretac™ implant (Acufex Microsurgical, Inc., Norwood, Mass.) is described as an absorbable tack of a synthetic polyglyconate copolymer. (*Arthroscopy* 11(2):194–198 (1995).) Additionally, European Patent No. 0412280 describes a pin made of poly (L-DL-lactide). However, neither of these devices is both resorbable and swellable.

The implant body which comprises the principle component of the implant device of the present invention is preferably formed from a dehydrated crosslinked collagen matrix. Collagen matrices have been previously described for various uses. See, for example: U.S. Pat. Nos. 5,162,430; 5,324,775; 5,328,955; 5,475,052; 5,523,348; 5,304,595; 5,306,500; 5,376,375; 5,413,791; and 5,446,091. In the field of tissue treatment, collagen-containing materials have been described for use in soft tissue repair (U.S. Pat. Nos. 4,424,208 and 4,582,640.) As described therein, these materials were used in the form of injectable aqueous dispersions of collagen gels.

Additionally, U.S. Pat. Nos. 4,563,350 and 4,888,366 describe the use of lyophilized ('350) and preformed ('366) collagen carriers of osteoinductive factors in bone repair. When used as preformed solid implants, these carriers consist generally of ceramic materials which are held together by collagen. Similarly, U.S. Pat. No. 4,776,890 describes non-crosslinked collagen/mineral implants, which can be moistened and molded into a desired shape before implantation. Therein, crosslinking is described as being undesirable because of its inhibitory effects on bone ingrowth. Also, U.S. Pat. Nos. 4,795,467, 5,035,715 and 5,110,604 describe porous collagen-containing implants for use in bone repair and/or wound healing.

Uniformly shaped swellable devices made from polymeric materials are not easily manufactured. This is due in part to the fact that in order to be swellable, it is generally necessary for the polymeric material to be preformed while "wet," then dried to effect shrinkage. When the material is rewetted, it will thus have a tendency to swell in size. However, the drying process is not easily controlled and often results in formation of irregularly and irreproducibly shaped materials. Accordingly, there is a need to provide methods and apparatuses for making swellable, uniformly shaped devices from polymeric materials. The present invention therefore relates to methods and apparatuses for making such devices using extrusion molding, and more particularly to collagen-containing devices which, when dried, have uniform shape, and have predetermined swelling characteristics.

Shaped collagen-containing products and methods of making shaped collagen-containing products are known. Common methods for fabricating shaped collagen include film-forming methods, such as the casting of a lenticular device defined by a mold as disclosed in U.S. Pat. No. 5,322,648. In addition, U.S. Pat. No. 5,501,706 discloses a shaped medical implant structure which is shaped using a containment member. Extrusion is also used to form shaped collagen products. For example, U.S. Pat. No. 4,923,380 discloses a method for extruding a reactive collagen gel through a spinneret into a coagulating bath to create a collagen tubule suitable for prosthetic and nerve-suture applications. A shaped product is also formed by extruding a collagen-containing precursor mixture into a coagulating solution and subsequently freezing to achieve the final shaped collagen product as disclosed by U.S. Pat No. 4,533,358.

Although the aforementioned patents and publications address to some extent how to produce shaped collagen-containing products for medical purposes, there exists a need for improved methods of producing dried, swellable, uniformly shaped collagen-containing products which do not require processing steps that are expensive or involve numerous solvent treatments.

The present invention relates to the use of dense, preformed hard tissue implants comprising a crosslinked implant body which is both resorbable (i.e. it is replaced by ingrowth of tissue) and swellable. Because the implant body swells after insertion, the implant becomes anchored in place, which eliminates the necessity for anchoring structures such as barbs, fins and wings. Additionally, because the implant body is dense when implanted and thereafter rendered less dense by degradation, it can initially provide adequate mechanical integrity while later serving as a scaffold for tissue ingrowth.

The implants of the present invention are placed within the hard tissue to increase its load bearing capacity, and/or to serve as a site for attachment of a second tissue. Also, by combining the use of these implants with other surgical devices such as sutures, screws, pins and rods, the effectiveness of tissue repair can be greatly enhanced.

The present invention also relates to apparatuses and methods for manufacturing implants, as well as polymer devices which are suitable for use in non-medical applications which, like the implants, are uniformly shaped and swellable.

SUMMARY OF THE INVENTION

In accordance with one aspect of the present invention, a hard tissue implant is described which increases the load bearing capacity of the hard tissue into which it is implanted. The implant consists of a resorbable, swellable implant body of a dehydrated crosslinked biocompatible polymer. In a preferred embodiment, the implant consists of an elongated cylindrical implant body, and a load-distributing device which is adapted to fit at one end of the implant body. The load-distributing device serves as an attachment site for a suture which is threaded through a hollow channel that runs through the entire length of the implant body.

The implant body may have a smooth exterior surface, or it may have an enhanced surface morphology. In particular, the implant may be pitted, textured or ribbed on its exterior surface to enhance fixation into the hard tissue.

The implant dimensions will be determined in accordance with the particular use to which the implant will be put. Generally, the implant body is elongated, i.e. it is longer than it is wide. For use in the repair of a rotator cuff, the implant is preferably between about 1.0 mm and about 6.0 mm wide, and between about 3.0 mm and about 30 mm long, more preferably between about 2.0 mm and about 5.0 mm wide, and between about 5.0 mm and about 20.0 mm long, most preferably between about 2.5 mm and about 4.5 mm wide, and between about 8.0 mm and about 18.0 mm long.

The implant body is formed from a biocompatible polymer which has been crosslinked, either covalently or noncovalently, into a three dimensional matrix. In a preferred embodiment, the biocompatible polymer is crosslinked by reacting it with a crosslinking agent. Particularly preferred crosslinking agents are the aldehyde-containing crosslinking agents, such as glutaraldehyde and formaldehyde. Alternatively, the crosslinking agent may be a functionally activated synthetic hydrophilic polymer, or a mixture of an aldehyde-containing crosslinking agent and a functionally activated synthetic hydrophilic polymer. The functionally activated synthetic polymer can be a multifunctionally activated polyethylene glycol, such as SG-PEG or SE-PEG. In yet another embodiment, crosslinking may be achieved by non-chemical methods such as drying, irradiation, heating or compression.

The biocompatible polymer can be any of a number of polymers which are capable of forming a crosslinked three-dimensional matrix that is both resorbable and swellable after drying. Preferably, the biocompatible polymer is collagen, and more preferably it is fibrillar collagen.

In addition to the biocompatible polymer (and optional crosslinking agent), the implant body may also contain particulate material, such as particulate collagen, poly(lactic acid), poly(glycolic acid), polytetrafluoroethylene, silicone rubber, calcium carbonate, calcium sulfate, and silicon carbide. A preferred particulate material for inclusion in the implant body is calcium phosphate ceramic particles, such as tricalcium phosphate and hydroxyapatite, or a mixture of tricalcium phosphate and hydroxyapatite.

Alternatively, the implant body may also include one or more biologically active agents, such as a growth factor, and in particular, a member of the transforming growth factor supergene family.

Also in accordance with the present invention is a process for preparing an implant body for use in a load bearing implant device for hard tissue repair in the body of a mammalian subject comprising the steps of:

(a) mixing together a biocompatible polymer with a crosslinking agent to form a reaction mixture;

(b) introducing the reaction mixture into a mold having a desired shape before substantial crosslinking has occurred between the biocompatible polymer and the crosslinking agent;

(c) allowing the biocompatible polymer and the crosslinking agent to react within the mold to form a matrix; and (d) drying the matrix to a moisture content of 20% or less by weight to form a dehydrated implant body.

This process can be utilized to prepare any of the aforementioned embodiments of the implant body of the present invention.

Another aspect of the present invention is a method for joining a second tissue to a first hard tissue which involves the steps of:

(a) forming a cavity in the first tissue;

(b) inserting a load bearing implant into the cavity, wherein the implant comprises:

(i) a resorbable, swellable implant body comprising a dehydrated crosslinked biocompatible polymer; and (ii) a load-distributing device adapted to fit at one end of the implant body to hold a suture;

(c) allowing the implant body to rehydrate in situ to anchor the implant into the first tissue; and (d) attaching a second tissue to the implant using the suture.

In yet another aspect of the present invention, the implant can be used in a method for anchoring a surgical device into a hard tissue, which method involves the steps of:

(a) forming a cavity in the hard tissue;

(b) inserting a load bearing implant into the cavity, wherein the implant comprises a resorbable, swellable implant body comprising a dehydrated crosslinked biocompatible polymer;

(c) inserting the surgical device into the implant; and (d) before or after step (c), allowing the implant body to rehydrate in situ to anchor the implant into the hard tissue.

In still another aspect of the present invention, the implant can be used in a method to secure a first hard tissue to a second hard tissue, which method involves the steps of:

(a) inserting at least one load bearing implant into the hard tissues, such that each load bearing implant traverses both of the hard tissues, wherein the load bearing implant comprises a resorbable, swellable implant body comprising a dehydrated crosslinked biocompatible polymer, and (b) allowing the implant body to rehydrate in situ to anchor the implant into the first and second tissues.

A further aspect of the present invention relates to methods and apparatuses for making dried, swellable, uniformly shaped polymer bodies which can be used for mechanical and industrial applications as well as in the medical field. The polymer bodies which are made therefrom exhibit physical properties that give rise to enhanced drying and swelling characteristics.

In one embodiment, the method for making a polymer body comprises the steps of: forming a viscous suspension or solution (i.e. a mixture) of a polymer; extruding the mixture through a mold die into a mold to form a polymer matrix, wherein the mold die has a central axis and at least three ribs extending in an outward direction from the central axis; then drying the matrix to form the polymer body. This method can be used to prepare a polymer body from any of the aforementioned compositions which were useful for making implant devices.

In a preferred embodiment for making implant devices, the mold contains a mandrel through the mold cavity, so that the implant body formed with such a device will have a channel running through it for holding a suture.

In another embodiment, the apparatus for making the polymer body comprises a mold die as previously described, and a mold which is adapted for extrusion of the polymer mixture into the mold.

The polymer bodies that are made according to the aforementioned method comprise polymer molecules having a uniform orientation along the longitudinal axis and areas having a different orientation across the cross-section. These areas differ in the degree in which the polymer molecules are oriented parallel to the longitudinal axis. Such polymer bodies exhibit uniform swelling rates along the longitudinal axis and areas having different swelling rates across the cross-section, with those areas which correspond to polymer molecules oriented parallel to the longitudinal axis demonstrating less swelling than those areas which are less oriented in this manner.

Other aspects of the present invention are described throughout the specification.

BRIEF DESCRIPTION OF THE DRAWINGS

FIG. 1 is a perspective view of a representative embodiment of the implant of the present invention.

FIG. 3b is a cross-section of the implant body of FIG. 3a.

FIG. 4b is a cross-section of the implant body of FIG. 4a.

FIGS. 5a–g are perspective views of the employment of the implant depicted in FIG. 1 as follows:

FIG. 5a depicts a hard tissue.

FIG. 5b depicts the hard tissue in relation to an awl to be used to form a cavity in the hard tissue.

FIG. 5c depicts the hard tissue after formation of a cavity.

FIG. 5d depicts the implant being inserted into the hard tissue via an insertion device.

FIG. 5e depicts the implant during insertion into the hard tissue.

FIG. 5f is a perspective view of the implant immediately after insertion.

FIG. 5g is a perspective view of the implant after swelling.

FIG. 6a depicts the implant after insertion into a hard (first) tissue and swelling.

FIG. 6b depicts the implant in relation to a soft (second) tissue to be attached to the hard tissue.

FIG. 6c depicts the attachment of the second tissue to the first tissue via a suture.

FIG. 7a is a perspective view of a representative embodiment of a load-distributing device.

FIG. 7b is a cross-section of the load-distributing device depicted in 7a.

FIG. 7c is a perspective view of another representative embodiment of a load-distributing device.

FIG. 7d is a cross-section of the load-distributing device depicted in 7c.

FIG. 7e is a perspective view of still another representative embodiment of a load-distributing device.

FIG. 7f is a cross-section of the load-distributing device depicted in 7e.

FIG. 8a is a perspective view of a representative embodiment of a load-distributing device having a complex shape.

FIG. 8b is a cross-section of the load-distributing device depicted in 8a.

FIG. 8c is a side view of the load-distributing device depicted in 8a.

FIG. 8d is a cross-section of a representative embodiment of the implant which utilizes the load-distributing device depicted in FIGS. 8a–c.

FIG. 12 also depicts a standard syringe for which the apparatus is adapted to extrude a polymer material into the mold through the mold die.

FIGS. 15a–h depict the various steps which are employed for formation of a polymer body using the apparatus depicted in FIG. 1.

FIG. 15a is a cross-section of the apparatus (and a side view of the syringe containing the polymer material) before extrusion of the polymer material through the mold die into the mold.

FIG. 15b is the same view after extrusion of a portion of the polymer material through the mold die into the mold.

FIG. 15c is the same view after all of the polymer material is extruded through the mold die into the mold.

FIG. 15d is the same view after disassembly of the mold from around the polymer matrix.

FIG. 15e is a cross-section of a drying oven containing the polymer matrix vertically suspended therein.

FIG. 15f is the same view after the polymer matrix has been dried to form a swellable polymer body.

FIG. 15g is the same view after separation of the polymer body.

FIG. 15h is the same view during cutting of the polymer body to the desired length.

FIG. 16a is a cross-section of the mold die.

FIG. 16b shows the appearance of the undried polymer body under normal fluorescent light.

FIG. 16c shows the appearance of the same undried polymer body under polarized light.

FIG. 16d shows the polymer body after drying.

DETAILED DESCRIPTION OF THE PREFERRED EMBODIMENTS OF THE INVENTION

Figure 2A:
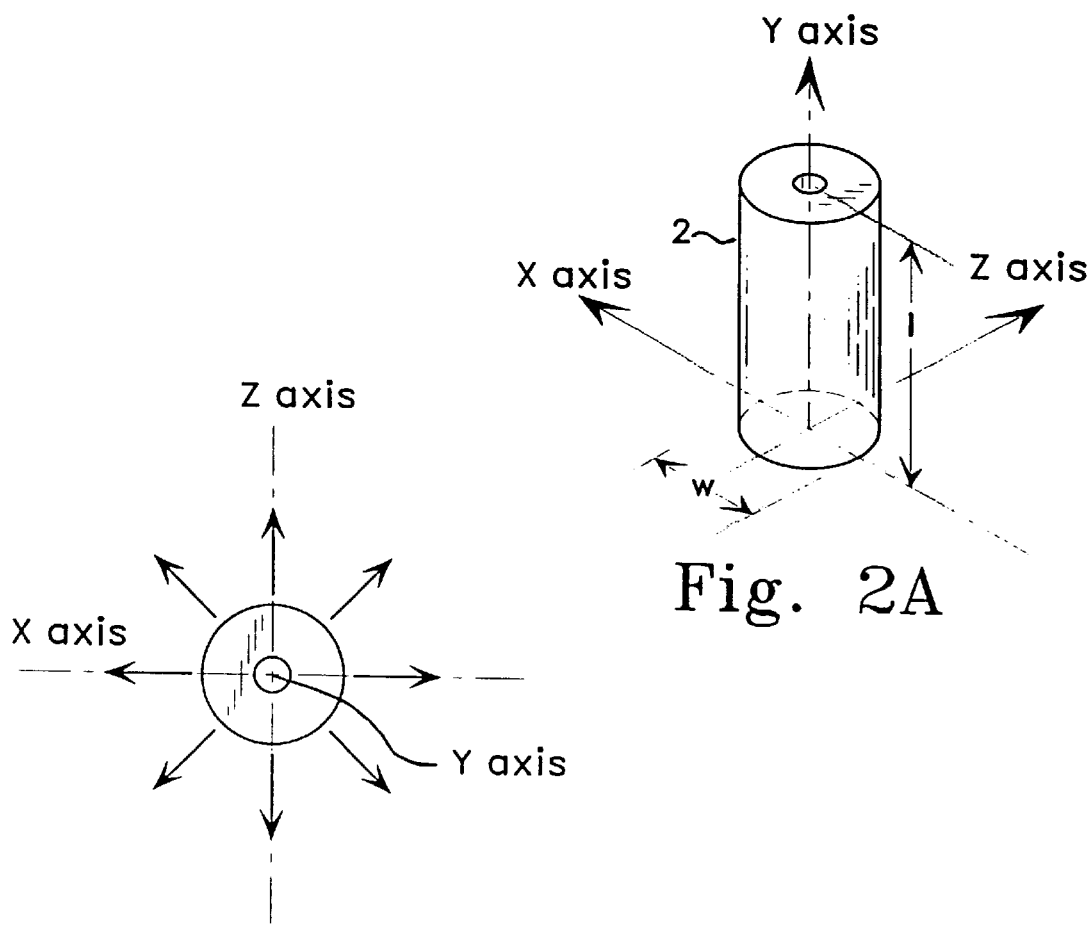
FIG. 2a is a perspective view of the implant body of the implant depicted in FIG. 1 which further depicts the width (w) and length (l) of the implant body as they relate to the x and the y axis, respectively.

The present invention relates to uniformly shaped, swellable devices made from polymeric materials. In a preferred embodiment of the present invention, the uniformly shaped devices are adapted for use as implants in tissue repair. More specifically, the implants impart enhanced load bearing capacity to hard tissue, which increases the load that can be put on the hard tissue during the repair process. In particular, the implants of the present invention may be useful for securing or joining a second (hard or soft) tissue to a first (hard) tissue. Additionally, the implants may be useful in anchoring a surgical device, such as a screw or pin, into a hard tissue.

The implant of the present invention comprises a dehydrated, resorbable, swellable preformed body of a crosslinked matrix material. One feature of the implant body is that it becomes anchored in place after insertion due to swelling upon rehydration, rather than by means of mechanical anchoring, such as protruding barbs and fins. This swelling fills the site of insertion in the hard tissue, which can compensate for any irregularities in the shape of the cavity. Another feature of the implant body is that it is eventually resorbed. In general, by the time the implant body has completely resorbed, the site that the implant body occupied will have been replaced by native tissue. Because the implant body is eventually resorbed by the body and replaced by native tissue, a second surgery to remove the device is not necessary. Also, in the event of a recurrent injury, the same site may be used to implant another device.

In addition to the implant body thus described, the implant may also optionally incorporate other devices, such as load-distributing devices, surgical screws, pins, etc. As used herein, the term "implant" refers to the entire device to be inserted into the hard tissue, and the term "implant body" refers to the portion of the implant consisting of the preformed crosslinked matrix. See, for example, FIG. 1, which depicts a preferred embodiment of the implant (1), and shows the relationship between the implant body (2), and an optional load-distributing device (3) which is used to distribute the load put upon the implant body (2) when the suture (4) is pulled.

As described in greater detail below, the devices which are made in accordance with the present invention are formed by extruding a matrix material through a mold die into a mold to produce a preformed "polymer matrix," which is subsequently dehydrated to form a polymer body. The matrix (and thus the polymer body) may also include optional components, such as biologically active agents.

Matrix Materials

The choice of matrix material will necessarily depend on the application for which the device will be used. For example, in order to prepare an implant body for in vivo applications, it is first necessary to provide a biocompatible polymer which serves as the matrix material. Depending on the matrix material selected, it may also be necessary to provide a chemical crosslinking agent. In a preferred embodiment, collagen serves as the matrix material. Collagen is the major protein component of bone, cartilage, skin, and connective tissue in animals. Collagen in its native form is typically a rigid, rod-shaped molecule approximately 300 nanometers (nm) long and 1.5 nm in diameter. It is comprised of three collagen polypeptides which form a tight triple helix. The collagen polypeptides are characterized by a long midsection having the repeating sequence -Gly-X-Y-, where X and Y are often proline or hydroxyproline, bounded at each end by the "telopeptide" regions, which constitute less than about 5 percent (%) of the molecule. The telopeptide region of the collagen chains are typically responsible for the crosslinking between chains and for the immunogenicity of the protein.

In general, collagen from any source may be used in the practice of the present invention. For example, collagen may be extracted and purified from human or other mammalian source, such as bovine or porcine corium and human placenta, or may be recombinantly or otherwise produced. The preparation of purified collagen in solution from bovine skin is basically a three-step process involving solubilization, enzyme treatment, and purification, as described in U.S. Pat. Nos. 4,140,537 and 4,488,911. Additionally, U.S. Pat. No. 5,428,022 discloses methods of extracting and purifying collagen from the human placenta PCT Publication No. WO 94/16570 discloses methods of producing recombinant human collagen in the milk of transgenic animals, including transgenic cows.

Collagen of any type, including, but not limited to, types I, II, III, IV, or any combination thereof, may be used, although type I is generally preferred. Either atelopeptide or telopeptide-containing collagen may be used. However, when collagen from a xenogenic source, such as bovine collagen, is used, atelopeptide collagen is generally preferred, because of its reduced immunogenicity compared to telopeptide-containing collagen. The term "collagen" or "collagen material" as used herein refers to all forms of collagen, including those which have been processed or otherwise modified.

Collagen for use in the present invention is typically available in an aqueous suspension (fibrillar collagen) or solution (nonfibrillar collagen) having a collagen concentration within the range of about 10 mg/ml to about 120 mg/ml, preferably, between about 20 mg/ml to about 90 mg/ml. Collagen in fibrillar form is preferably used in the practice of the present invention because of its expected superior strength and greater persistence in hard tissue compared to nonfibrillar collagen.

Although fibrillar collagen is generally preferred to prepare the implant bodies of the present invention, nonfibrillar collagen may be used in place of or in addition to fibrillar collagen. The term "nonfibrillar" collagen as used herein is intended to encompass collagen types that are nonfibrillar in native form (such as types IV, VI, and VII); collagen that has been rendered substantially nonfibrillar by the addition of one or more fiber disassembly agent; and collagen which has been chemically modified such that it is in substantially nonfibrillar form at or around neutral pH.

Fibrillar collagen may be rendered nonfibrillar by the addition of one or more fiber disassembly agents. The fiber disassembly agent should be present in an amount sufficient to render the collagen substantially nonfibrillar at pH 7. Agents capable of rendering collagen nonfibrillar include, without limitation, various biocompatible alcohols, amino acids, inorganic salts, and carbohydrates.

Collagens that have been chemically modified to be nonfibrillar at neutral pH include succinylated collagen and methylated collagen, both of which can be prepared according to the methods described in U.S. Pat. No. 4,164,559.

Other polymers which are suitable for use in forming uniformly shaped swellable devices include a wide range of synthetic and naturally occurring materials. In general, the polymers need only be capable of forming a polymer body which is both swellable, and sufficiently strong to withstand the mechanical load to which it is subjected after placement. Examples of polymer materials which are biodegradable and are suitable for use in forming implant bodies for tissue repair include, inter alia, polyesters, polyamides, polypeptides, poly(orthoesters), polyanhydrides, polysaccharides and proteins. Specific examples include elastin, chitin, chitosan, poly(lactic acid), poly (glycolic acid), dextran, methylated collagen, hyaluronic acid and copolymers thereof. Suitable polymers can be hydrophilic or hydrophobic.

The matrix may be formed from a single biocompatible polymer, or a mixture of two or more biocompatible polymers. For example, a synthetic hydrophilic polymer can be added to a suspension or solution of collagen to enhance the rate of hydration after implantation. In addition, the matrix may be formed from a polymer per se, or it may be formed from individual monomeric units which are at least partially polymerized before extrusion through the mold die as described below.

Crosslinking

Polymers which are used in the practice of the present invention should be capable of being crosslinked to form a three dimensional matrix. Crosslinking may be achieved by a variety of known chemical and non-chemical methods. Non-chemical methods include, inter alia, irradiation, drying, heating and compression. Preferably, crosslinking is achieved using chemical methods, which includes either ionic or covalent crosslinking. Covalent crosslinking can be achieved by functionalizing the matrix material, or by supplying a separate chemical crosslinking agent. As used herein, the term "crosslinking agent" refers to a chemical crosslinking agent. Crosslinking may also be achieved by a combination of two or more different mechanisms.

Suitable chemical crosslinking agents for use in the practice of the invention include, without limitation, glutaraldehyde, functionally activated synthetic hydrophobic or hydrophilic polymers, photoactivatable crosslinking agents, formaldehyde, divinyl sulfone, carbodiimide, epoxide, imidazole, and combinations thereof. The optimum ratio of crosslinking agent to matrix material will, of course, vary depending on the particular crosslinking agent used and the degree of crosslinking desired.

Aldehyde-containing crosslinking agents such as glutaraldehyde and formaldehyde are particularly preferred for use in formation of implant bodies for tissue repair, because the matrices thus formed have sufficient physical strength to withstand the various processing and handling steps (e.g., molding and drying). Also, once dried, a formaldehyde or glutaraldehyde crosslinked collagen matrix has sufficient strength to enhance the structural integrity of hard tissue. Methods for crosslinking collagen using glutaraldehyde are disclosed in U.S. Pat. Nos. 4,582,640 and 4,642,117. When aldehyde-containing crosslinking agents, such as glutaraldehyde or formaldehyde, are used in the practice of the invention, the amount of crosslinking agent is optimized to limit unbound crosslinker in the final product.

Functionally activated synthetic hydrophilic polymers can also be used as the crosslinking agent either alone or in combination with the aforementioned crosslinking agents. Methods for crosslinking matrix materials using functionally activated synthetic hydrophilic polymers are disclosed in U.S. Pat. Nos. 5,162,430 and 5,328,955. Multifunctionally activated synthetic polymers are disclosed in U.S. Pat. No. 5,328,955, which describes the use of difunctionally activated poly(ethyleneglycol)-bis-(succinimidyl glutarate) (SG-PEG) and difunctionally activated poly(ethyleneglycol)-bis-succinimidyl proprionic acid (SE-PEG).

Optional Components

Optional components can be incorporated into the devices at any stage during formation. For example, optional components can be added to either the polymer or the crosslinker before they are mixed together. Alternatively, they can be added to the reaction mixture at any stage during crosslinking. It is also possible to add optional components to the matrix after crosslinking at any stage of implant processing.

Particulate materials may also be incorporated into the device by incorporating them into the matrix material prior to crosslinking (or the matrix material-crosslinking agent mixture). The presence of a particulate material in the implant body may serve several functions, as follows: (i) it may aid in shape retention during dehydration of the implant; (ii) it may provide additional roughness to the surface of the implant body to aid in initial fixation of the implant into the hard tissue; and (iii) it may enhance resorbability of the implant by native tissue.

Particulate material may be any shape, such as spherical, elongated fibers, etc. In particular, fiber-shaped particles can be included in the reaction mixture and, because of their shape, they would be expected to be oriented in much the same way as the polymer material during extrusion.

Particulate materials for use in formation of implant bodies have a preferred particle diameter between about 50 to about 500 $\mu$m; more preferably, between about 75 to about 300 $\mu$m; most preferably, between about 100 to about 200 $\mu$m. Particulate materials are generally incorporated into the biocompatible polymer suspension at a concentration of about 50% wt./wt. or less particulate material/biocompatible polymer ratio. Higher concentrations of particulate material are not preferred, because such compositions will not generally shrink or swell to a sufficient degree to achieve the desired density and associated mechanical strength.

Suitable particulate materials for use in forming implant bodies include, without limitation, implant-grade biologically-derived polymers such as collagen; synthetic polymers such as poly(lactic acid), poly(glycolic acid), polytetrafluoroethylene; silicon carbide or silicone rubber; hydrogels; and ceramics or glasses such as calcium carbonate, calcium sulfate or other calcium salts. As used herein, the term "particulate materials" also refers to mixtures or copolymers containing two or more different types of particulate material, such as those listed above.

Preferred ceramic particles for use in forming implant bodies include calcium phosphate ceramics, such as tricalcium phosphate particles, hydroxyapatite particles, and mixtures thereof. For best results, the ceramic particles generally comprise spherical particles having a diameter within the range of about 100 microns to about 1000 microns.

Biologically active agents may also be incorporated into an implant body. The term "biologically active agent" as used herein refers to molecules which exert biological effects in vivo. Examples of biologically active agents include, without limitation, enzymes, receptor antagonists or agonists, hormones, growth factors, fluoride, antibiotics, antimicrobial agents, and antibodies. The term "biologically active agent" is also intended to encompass combinations or mixtures of two or more active agents, as defined above. The biologically active agents must also be capable of maintaining their activity in the final implant device.

Suitable biologically active agents for use in implant bodies include members of the transforming growth factor (TGF) supergene family, which are multifunctional regulatory proteins. Members of the TGF supergene family include the beta transforming growth factors (for example, TGF-1, TGF-2, TGF-3); bone morphogenetic proteins (for example, BMP-1, BMP-2, BMP-3, BMP-4, BMP-5, BMP-6, BMP-7, BMP-8, BMP-9); heparin binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

It is also within the present invention to include agents which enhance the visualization of the implanted device using various imaging techniques. Such agents include, inter alia, radiopaque agents, fluorine-containing chemicals, dyes, fluorescent substances and magnetically responsive compounds.

Other components which may be incorporated into the matrix include, without limitation, the following: polyethylene glycol (non activated), dextrose, glycerol, and glycosaminoglycans such as sodium hyaluronate, chondroitin sulfate and heparin.

Mixing the Matrix Components

In a representative method for preparing the preformed matrix, an aqueous suspension/solution of the matrix material is mixed with a chemical crosslinking agent to form a reaction mixture. For implant bodies that will be used in tissue repair, the matrix material is preferably present in the aqueous suspension/solution at a concentration within the range of about 10 to about 120 milligrams per milliliter of suspension/solution, preferably, between about 30 to about 90 milligrams per milliliter of suspension/solution.

The concentration of crosslinking agent used will depend upon a number of factors, including the particular crosslinking agent used, the concentration and type of matrix material used, and the degree of crosslinking desired. For example, when glutaraldehyde is used to prepare the implant body, the concentration of glutaraldehyde is generally within the range of about 8 to about 40 micrograms of glutaraldehyde per milligram of matrix material (e.g., when a collagen suspension/solution having a collagen concentration of 35 mg/ml is used, the concentration of glutaraldehyde used to crosslink the collagen would be in the range of about 280 micrograms to about 1.4 milligrams per milliliter of collagen suspension/solution; when a collagen suspension/solution having a collagen concentration of 65 mg/ml is used, the concentration of glutaraldehyde would be about 520 micrograms to about 2.6 milligrams per milliliter of collagen suspension/solution).

The collagen and crosslinking agent are preferably mixed so that the crosslinking agent is homogeneously dispersed with the matrix material suspension/solution. The collagen and crosslinking agent may be mixed, for example, using syringe-to-syringe mixing. The amount of mixing and mixing method chosen necessarily depends on the matrix material and crosslinking agent, as well as their relative concentrations, and can easily be determined and optimized by one of skill in the art.

Molding the Matrix

After the matrix material and crosslinking agent have been adequately mixed to achieve a relatively homogeneous reaction mixture, the reaction mixture is introduced into a mold, in which the matrix material and crosslinking agent are allowed to crosslink to form a matrix having the shape of the mold. Alternatively, the reaction mixture can be introduced into the mold and then crosslinked using known methods. Preferably, the matrix material and crosslinking agent are incubated within the mold until complete crosslinking is achieved. The reaction mixture may be incubated at elevated temperature (preferably, no greater than 37° C.) to accelerate the crosslinking reaction. The incubation time is a function of reaction mixture component concentrations and temperature, and can be easily optimized.

As described below under "Shaping the Matrix," the preferred method for introducing the reaction mixture into the mold is via extrusion through a specially designed mold die.

After complete crosslinking has been achieved (excluding additional crosslinking which may take place during drying), the resulting matrix is preferably removed from the mold and washed to remove any salts and excess, unreacted crosslinking agent. Washing may be performed, for example, by soaking the preformed matrix in deionized water overnight, preferably at room temperature or under refrigeration at 2–4° C.

Dehydrating the Preformed Matrix to Form the Polymer Body

The swellable polymer body is formed by drying the matrix, preferably until it has a moisture content of 20% or less by weight (i.e. until it is "dry") and more preferably less than 15%. For example, the matrix may be dried in an oven at 37° C., which generally requires a minimum of 12 hours, preferably 18–24 hours. Suitable moisture content will necessarily depend on the desired amount of swelling of the polymer body during use, and can easily be determined by preparing polymer bodies with different moisture contents and choosing the appropriate moisture content for the given application. Preformed matrices containing particulate materials generally require shorter drying times. To give the polymer body a certain predetermined shape, it may also be possible to further shape the preformed matrix during the drying process.

Upon drying, the matrix should exhibit a sufficient amount of shrinkage due to moisture loss during the drying process to allow adequate swelling to occur during rehydration to meet the needs of a given application. For example, if the swellable polymer body is being used as a hard tissue implant body, the amount of shrinkage during drying will be that which permits a sufficient degree of swelling after implantation to anchor the implant in place. Generally, the matrix should shrink to less than 80%, preferably to less than 50%, and most preferably to between 10% to 25% of its original volume. An elongated matrix will generally shrink to between 10% to 50% of its original diameter, and may also shrink to between 80% to 95% of its length. For example, an elongated matrix prior to drying may have a diameter of 11 mm and a length of 100 mm, but will shrink to about 2.8 to 5.5 mm in diameter and about 80 to 95 mm in length upon drying.

The polymer body may be manufactured under aseptic conditions or terminally sterilized following the dehydration step using e-beam or gamma irradiation.

Polymer Body Morphology

The morphology of the polymer body depends entirely on the purpose for which it will be used. In order to optimize fixation by swelling, a preferred polymer body shape is one which has a width, w (x-axis) and length, l (y-axis) as depicted in FIG. 2a, wherein the length is greater than the width. In the case of a cylindrically-shaped implant body, the width is equivalent to its diameter, such that when the implant (1) is inserted lengthwise into the hard tissue (2) as depicted in FIG. 2c, the majority of the swelling occurs radially (in an outward direction from the y-axis) as depicted in FIGS. 2b and 2c, thus resulting in a general increase in its diameter.

Figure 2B:
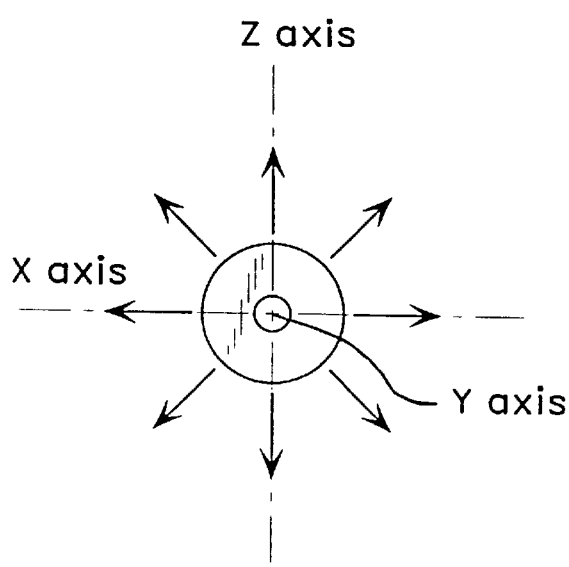
FIG. 2b shows a top view of the implant body depicted in FIG. 2a which shows the direction of swelling.
Figure 2C:
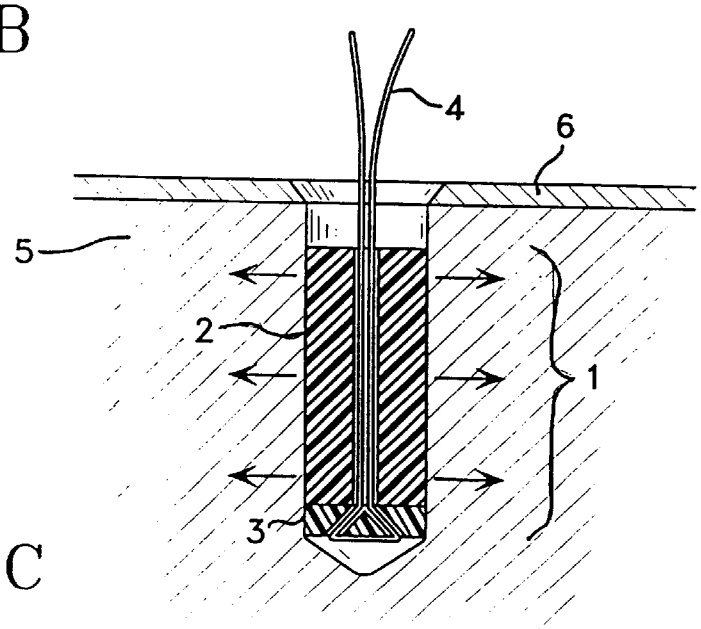
FIG. 2c is a cross-section of the implant depicted in FIG. 1 after placement in a hard tissue, which shows the direction of swelling.

Although depicted in FIGS. 2a–c as having a cylindrical shape, the polymer body may also have any oblong or irregular shape which is generally elongated (i.e. the greatest dimension of the polymer body along the y axis (i.e. its length) is greater than the greatest dimension in a plane perpendicular to the y axis (i.e. its width)).

The shape of the polymer body may be formed using a mold of a particular shape, or it may be formed after molding. Using an appropriate mold, no further sculpting of the implant body may be necessary. However, it is possible and sometimes desirable to use a mold that exceeds the desired finished dimensions of the preformed matrix, in which case the resulting matrix (or polymer body after drying) may be cut or sculpted to the desired size or shape.

The polymer body may be texturized (e.g., dimpled, pitted or ribbed) to give it an enhanced surface morphology. For example, the matrix can be texturized before, during or after drying. In particular, the outer surface of the implant body can be machined in such a manner as to create a texturized surface after drying. As used herein, the term "enhanced surface morphology" refers to a matrix (or an implant body formed therefrom) having an exterior surface that is not smooth. For example, it may be dimpled, pitted, or ribbed, or otherwise textured so as to increase the surface area of the implant body. This may serve to increase the rate of rehydration of the polymer body, which in turn results in an increased swelling rate. In the case of an implant body being inserted into a hard tissue, the enhanced surface morphology may also increase the friction between the implant body and the hard tissue to aid in anchoring the implant body into the hard tissue.

Figure 3A:
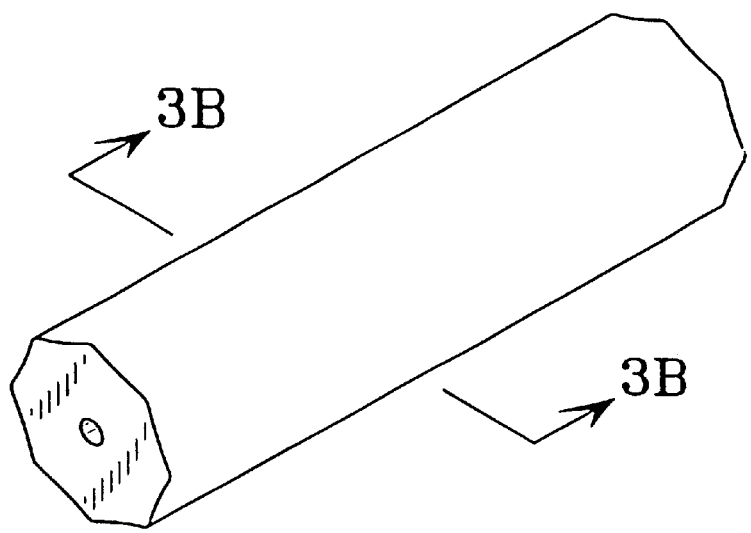
FIG. 3a is a perspective view of a representative embodiment of the implant body of the present invention.
Figure 3B:
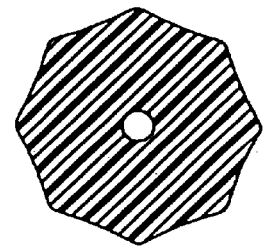

More particularly, if the implant body has edges or protrusions extending outward from a generally cylindrical surface, these edges or protrusions may compress upon insertion to provide an interference fit (i.e. a fit which results in enhanced fixation due to the force of the outer surface of the implant body upon the inner surface of the cavity). See FIG. 3a which depicts a perspective view, and 3b which depicts a cross-section of an implant body having 8 edges extending radially outward from the cylindrical surface of the implant body and running the entire length of the implant. In this example, the cross-section of the implant body is generally octagonal in shape, and the edges result from the intersections of the sides of the octagon. Also depicted therein is a central core which extends longitudinally through the implant through which a suture can be threaded.

Figure 4A:
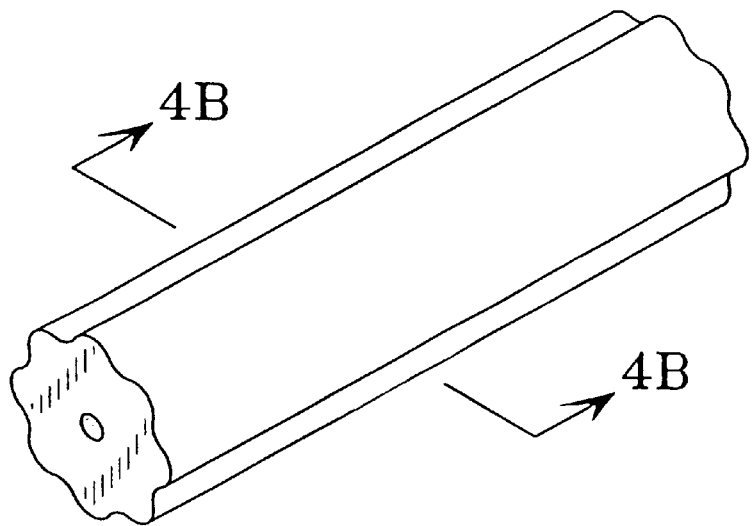
FIG. 4a is a perspective view of another representative embodiment of the implant body of the present invention.
Figure 4B:
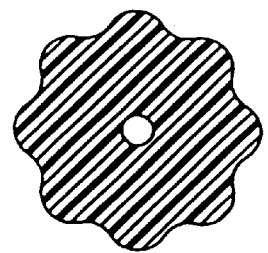

A perspective view of an alternative embodiment is depicted in FIG. 4a. As shown in the cross-section depicted in FIG. 4b, this implant body has protrusions in the form of ribs which run the entire length of the implant body.

In addition, to facilitate insertion, the end of the implant to be inserted may be tapered (e.g., pointed or bullet-shaped) to facilitate driving the implant into the insertion site.

Dimensions of Implant Bodies for Tissue Repair

In one example, the polymer bodies which are made according to the present invention are used to repair a rotater cuff. For this particular use, the dimensions of the implant body are preferably between about 1.0 to about 6.0 mm in diameter and between about 3 to about 30 mm in length; more preferably, between about 2.0 to about 5.0 mm in diameter and between about 5 to about 20 mm in length; most preferably, between about to about 2.5 to about 4.5 mm in diameter and between about 8 to about 18 mm in length.

For other uses, the polymer body will necessarily have different dimensions that would be determined on the basis of their intended purpose.

Other Devices Used with an Implant Body for Tissue Repair

The implant body can be used alone in the practice of the present invention, or it can be used in conjunction with a load-distributing device, or other surgical devices such as screws, pins, etc. These additional devices can be incorporated into the implant body at any time before or after its formation. For example, a surgical pin can be placed within the mold, in which case the preformed matrix and resultant implant body would be formed with the pin already in place. Alternatively, the load-distributing or surgical device can be attached or inserted into the implant body after formation, but before insertion of the implant into the hard tissue.

In a preferred embodiment of the implant of the present invention, and as further described below, the implant comprises an implant body and a load-distributing device. As used herein, the term "load-distributing device" refers to a member which acts to distribute the mechanical forces placed on the implant body when the implant is being used to facilitate attachment of a first tissue to a second tissue. Such load-distributing devices may also be useful in other non-medical applications.

Inserting an Implant into a Hard Tissue

Figure 5A:
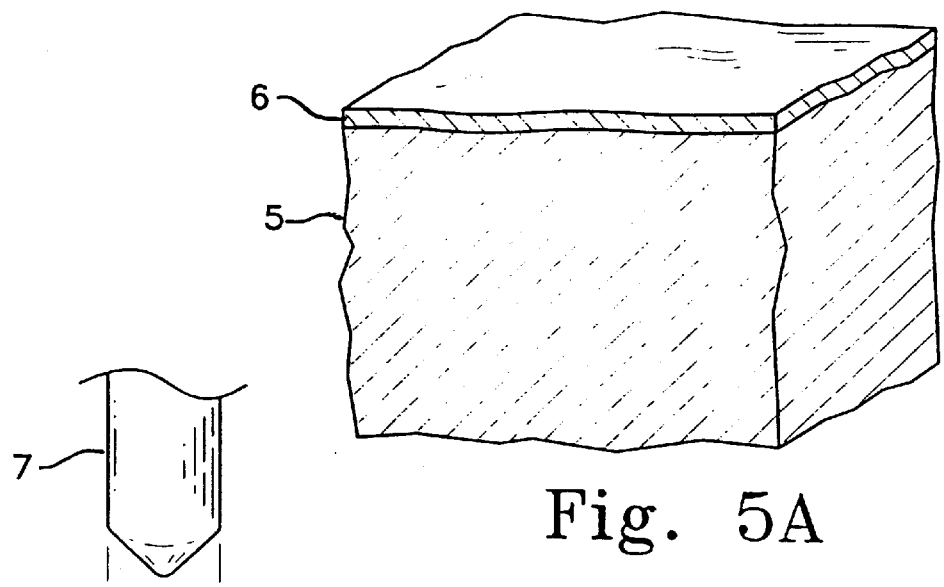
Figure 5B:
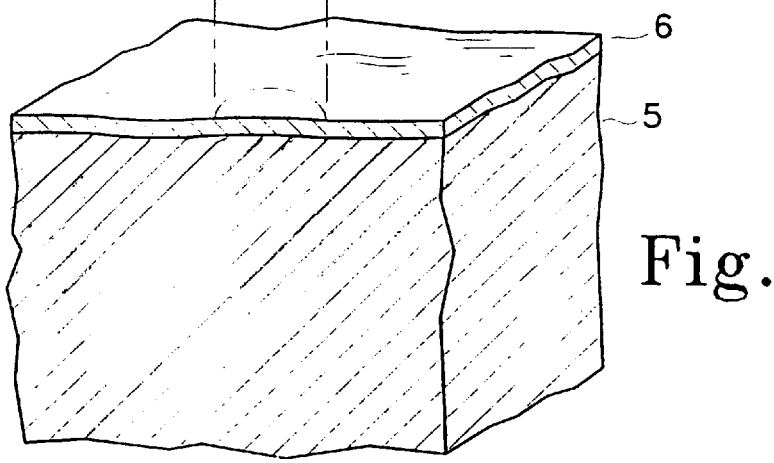
Figure 5C:
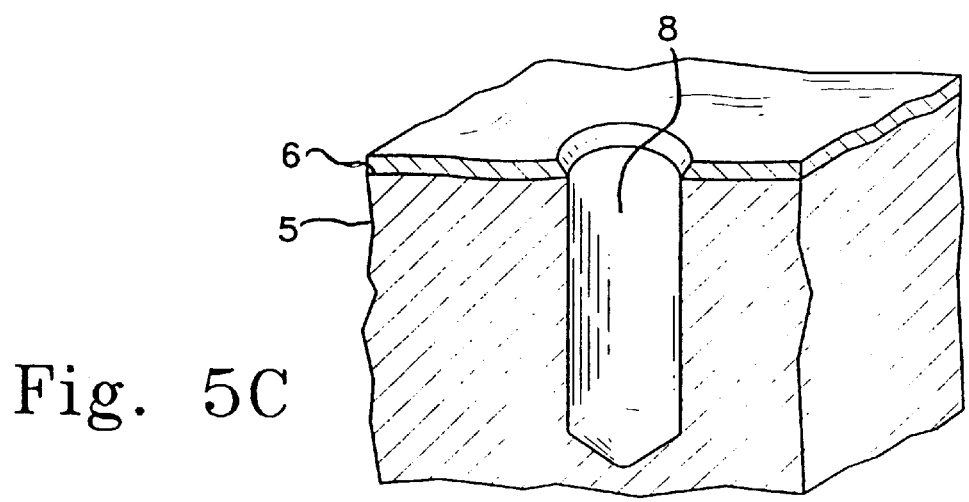
Figure 5F:
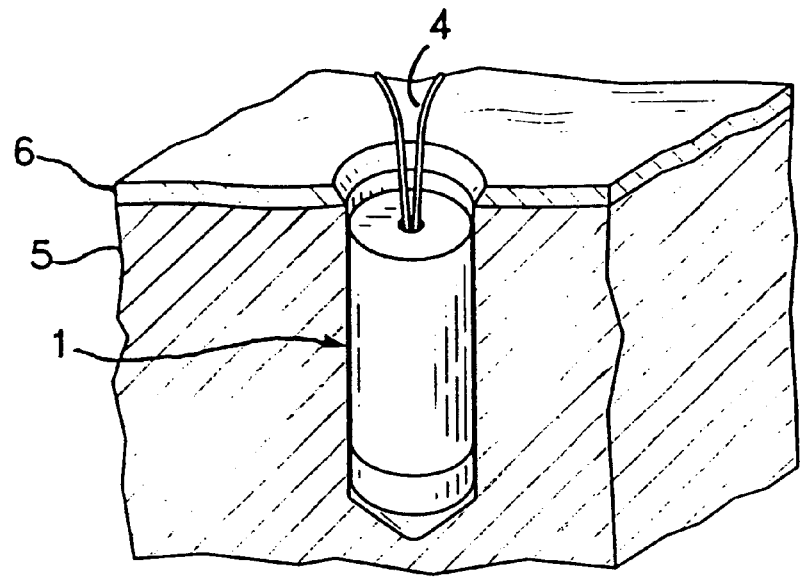
Figure 5G:
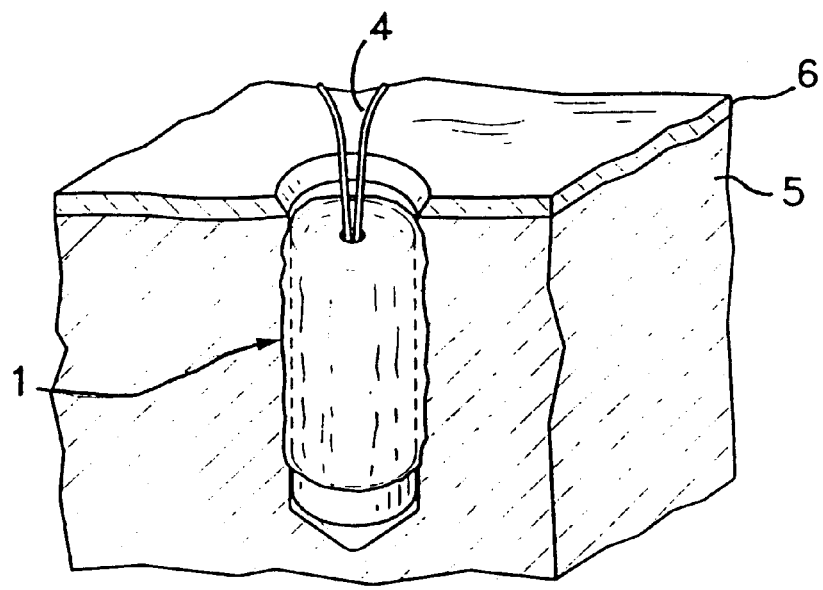

In order to insert an implant, a cavity is first formed in the hard tissue at the insertion site. As used herein, the term "hard tissue" refers to bone. A general method for insertion is depicted in FIGS. 5a to 5g. FIG. 5a shows the hard tissue (5) having a surface (6) into which the implant will be inserted. As depicted in FIG. 5b, the cavity is generally formed using a surgical drill or awl (7). FIG. 5c shows the cavity (8) thus formed. The implant (1) is then inserted manually into the cavity as depicted in FIGS. 5d and 5e using manual or mechanically induced pressure. Insertion of the implant may be facilitated by use of a specially designed insertion tool (9) and/or a mallet to drive the implant into the cavity. FIG. 5f shows the implant after insertion which is slightly below the surface (6) of the hard tissue (5). FIG. 5e shows the implant after the swelling of the implant body as depicted by an increase in diameter, but no substantial increase in length.

Generally, the diameter of the cavity (8) will approximate the diameter of the implant (1) to be inserted. However, to facilitate fixation, a cavity can be formed which is slightly smaller in diameter than the implant, which allows the implant to be press fit into the cavity. For best results, the inner diameter of the cavity should be approximately 0.1–0.5 millimeter less than the outer diameter of the implant, depending on the type and quality of the hard tissue. For example, when an implant having an outer diameter of 3.6 mm is used, the inner diameter of the cavity should be between about 3.1 to about 3.5 mm. Additionally, where the implant is generally cylindrical in shape and has protrusions extending outward as depicted in FIG. 3a–b and 4a–b, a cylindrical cavity is formed which has a diameter which approximates the smallest diameter of the insert. This diameter differential enhances the interference fit of the implant.

Using an Implant Body for Tissue Repair

The implant body should be dense enough to achieve the desired mechanical strength. By "dense," it is meant that the implant body is substantially compact, thus restricting its permeability to cells. As such, the implants of the present invention are different from the implants described in U.S. Pat. No. 5,110,604, which are not dense, but are porous. This means that the implant body will restrict tissue ingrowth until the implant body begins to degrade, after which it is capable of being infiltrated by tissue cells and replaced by tissue. In this way, strength can be optimized while still allowing for eventual resorption.

The load bearing implants of the present invention are particularly useful in porous bone, where a normal implant may not transfer load effectively to the bone. The entire implant swells, which means that the implant can accommodate larger imperfections of poorer quality bone. The implant after insertion and rehydration in situ preferably achieves a degree of fixation (ie. attainment of holding strength) soon enough to allow a surgeon to place a load on the implant during surgery without concern about dislodging the implant. In the ideal case, fixation occurs soon after placement of the device.

Types of surgical repairs that can be effected using the implants and methods of the present invention include, without limitation, repairs of the shoulder, endoscopic face lifts, collateral knee ligaments, cruciate knee ligaments, Achilles tendon, patellar tendon, hand, or wrist.

In a preferred embodiment of the present invention, the implant is used as a suture anchor to attach a second tissue to the hard tissue into which the implant is anchored. For use as such, the implant preferably has a hollow channel running through its length through which surgical suture can be threaded. To form the hollow channel, the mold used to form the implant body may contain at least one mandrel running the entire length of the mold. Alternatively, if the mold does not contain a mandrel, a hollow channel can subsequently be formed in the matrix or implant body formed therefrom by drilling or machining the channel after formation.

At least one standard surgical suture (e.g., Dacron #1 or #2 or braided polyester) is preferably threaded through at least one hollow channel in the implant (or in the matrix prior to drying). For example, one suture may be threaded through one channel; or several sutures may be threaded through the same channel; or several sutures may be threaded, one each, through several channels.

To prevent the suture from becoming disengaged from the implant, the suture may be knotted at the bottom of the implant. Alternatively, the implant may have attached thereto or associated therewith a load-distributing device, which may serve several functions: 1) it may distribute the mechanical forces on the implant; 2) it may prevent the suture from tearing or cutting through the implant; 3) it may aid fixation of the implant into the hard tissue; and 4) it may facilitate "suture slippage," i.e. allowing one end of the suture to slide relative to the other end during surgical procedures, which in turn facilitates complicated manipulations of sutures by surgeons, such as tying knots, especially through an arthroscopic portal (ie., the knot is tied in an accessible region and slid downward to anchor the tissue).

The load-distributing device and the implant body preferably come in contact over a fairly large area. In addition, it may be useful to provide cavities in the implant body which correspond to protrusions from the load-distributing device (or vice versa) to prevent the load-distributing device from rotating in a way that might erode the implant body surfaces in which it is in contact. In this regard, it may be desirable to form the matrix, or dry the matrix to form the implant body, with the load-distributing device already in place.

The necessary load bearing capacity of a suture anchor immediately after placement is determined by the forces required to tie the second tissue to the first tissue. In particular, if the second tissue is a retracted soft tissue, the implant must be capable of withstanding the forces necessary to bring the two tissues into close proximity. Since the implant will ultimately be exposed to the same types of forces as are exerted on the suture, the implant should be able to withstand (not be dislodged or damaged) as much forces as the suture for a desired length of time.

Figure 6A:
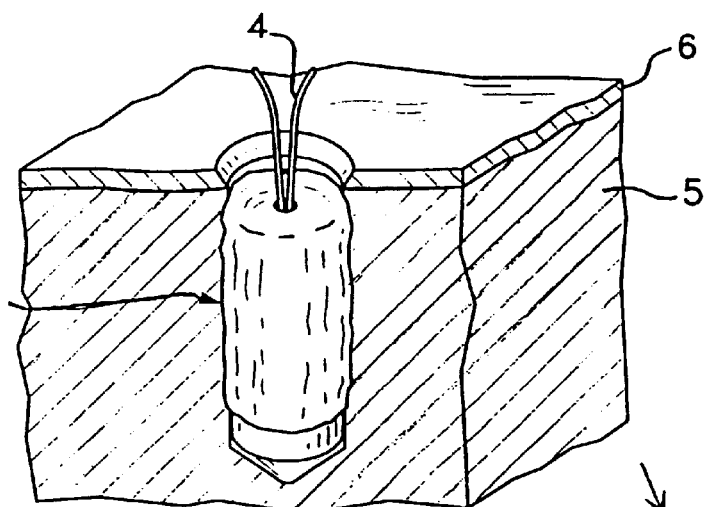
FIGS. 6a–c are perspective views of the employment of the implant depicted in FIG. 1 for use in attaching a second tissue to a first tissue as follows.
Figure 6B:
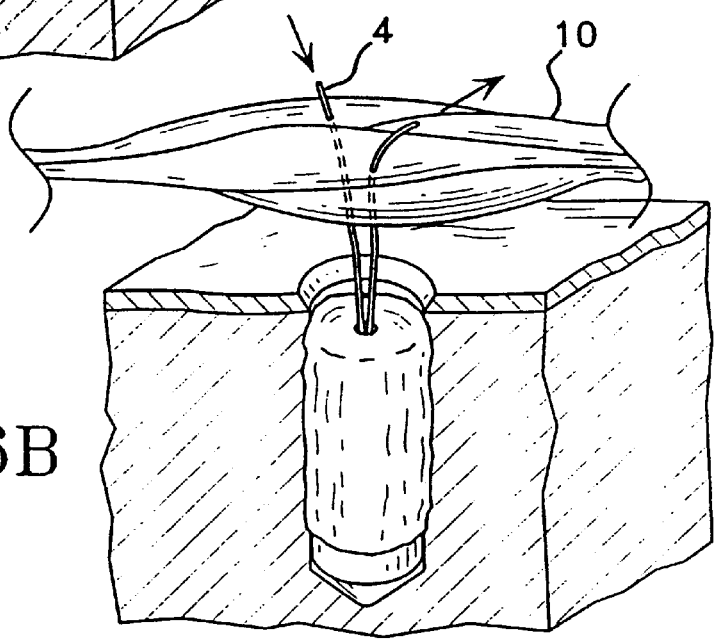
Figure 6C:
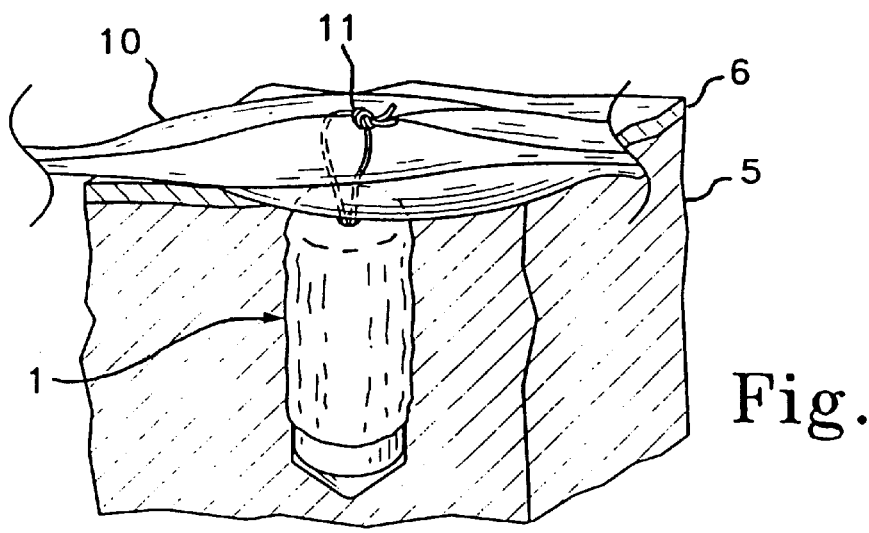

FIGS. 6a to 6c depict the use of an implant device to attach a soft tissue (10) to a hard tissue. As shown in FIG.

6a, the load-distributing device (3) is distal from the surface of the hard tissue (6). The suture (4) is threaded around (not shown) the load-distributing device, and is threaded through a hollow channel in the implant body (2). As shown in FIG. 6b, the suture is then threaded through the soft tissue (10). At this point, the suture can still be moved in either of the directions shown by the arrows in FIG. 6b, which is called "suture slippage." This slippage allows the soft tissue to be properly moved in place next to the hard tissue. Then, as depicted in FIG. 6c, the soft tissue (10) can be secured in place by putting a knot (11) in the suture. FIGS. 7a, c and e show perspective views of three different load-distributing device designs. FIGS. 7b, d and f show cross-sections of the same devices, respectively. As shown in FIGS. 7a and b, the load-distributing device may have a modified button-shape with two channels running through the device. The two "sides" of the button can be thought of as the two "ends" of the device. The two channels exit a single hole on one end of the device, and separate holes on the other end. This load-distributing device is also depicted in FIG. 2c. As shown, the end of the device with the single hole is next to the end of the insert body which is distal from the surface of the hard tissue This configuration is believed to facilitate load distribution.

FIGS. 7c and 7d show another embodiment of the load distributing device which is button-shaped. In this configuration, the load-distributing device has a hollow channel with a center bridging feature around which the suture is threaded. This configuration facilitates suture slippage. FIG. 7e and 7f shows yet another configuration of the load distributing device which consists of two separate members: a disc (12), and a mandrel attached thereto (13), where the mandrel has an eye (14) running through it at the end distal from the disc through which a suture can be threaded.

A preferred embodiment of the load-distributing device has a complex generally conical shape as depicted in FIGS. 8a to 8d. When in use as depicted in FIG. 8d, the end of the device having the smaller cone diameter will be distal from the implant body, and the end of the device having the larger cone diameter will be next to the implant body. As shown, the device has a center portion (15) which has a tear-drop shape. The suture is threaded around this center portion, and exits through a single opening (16). As additionally shown in FIGS. 8a to 8d, the device preferably has a continuous outer lip (17) in contact with the outer circumference of the implant body.

The load-distributing device may be manufactured from any medical grade ceramic (e.g., alumina, zirconia, hydroxyapatite), polymer (e.g., polysulfone, polymethyl methacrylate, ultra-high molecular weight polyethylene), metal (e.g., stainless steel or titanium), or composite material, but is preferably made from a material that is at least partially biodegradable, more preferably, fully biodegradable, such as a highly crosslinked collagen material.

Using the Implant Body Alone as a Tissue Implant

Figure 9A:
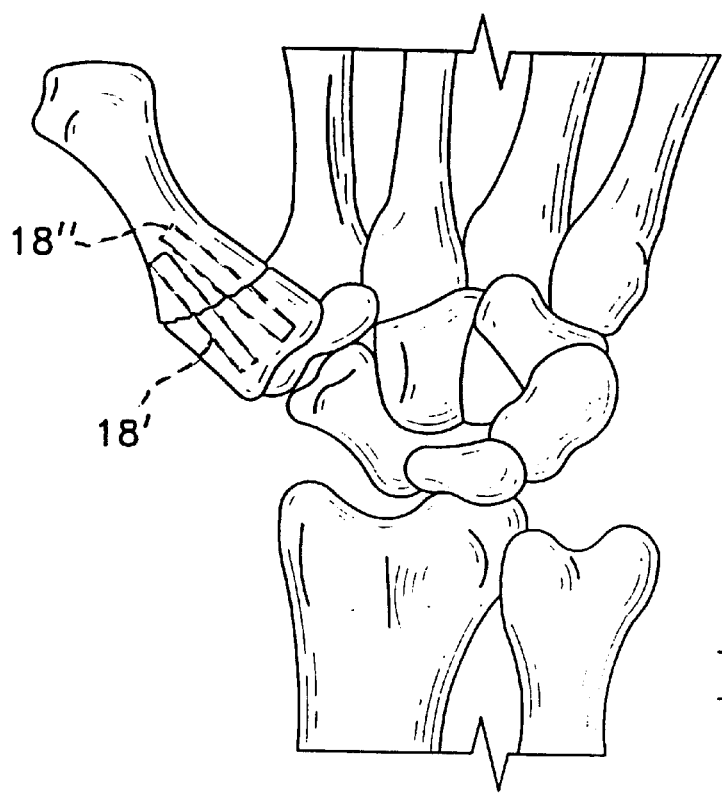
FIG. 9a is a graphical representation of a series of two of the implants of the present invention being used to secure a first hard tissue to a second hard tissue.
Figure 9B:
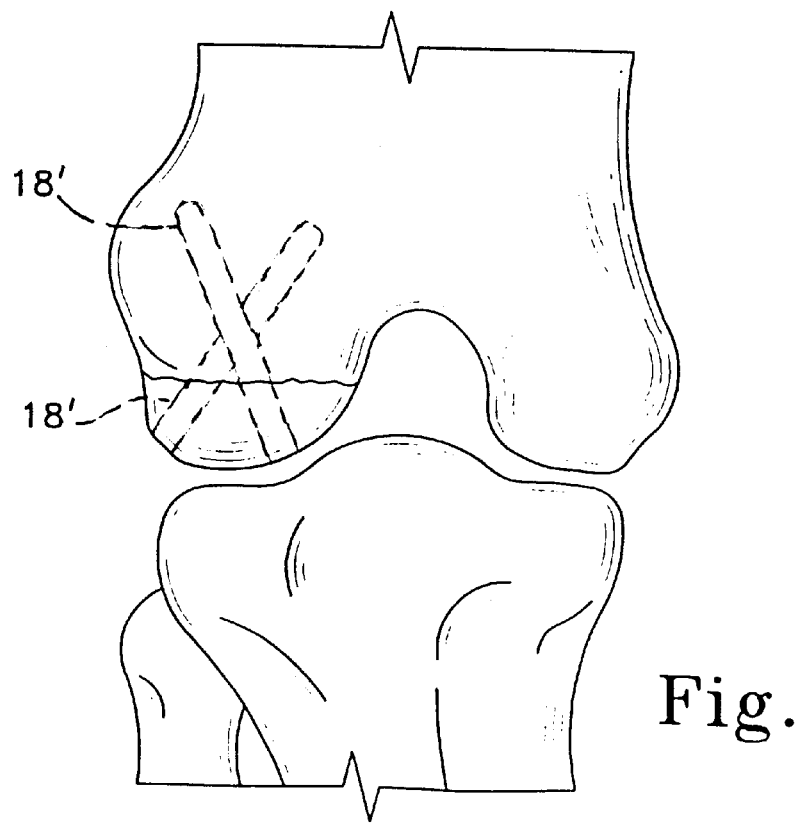
FIG. 9b is another graphical representation of a series of two of the implants made according to the present invention which are being used to secure a first hard tissue to a second hard tissue.

In accordance with the present invention, the implant body may also be used alone as an implant (i.e. inserted by itself without a load-distributing device or other surgical device attached thereto or associated therewith.) For example, the implant of the present invention may be used to secure two hard tissues together as depicted in FIGS. 9a and 9b and further described in Example 7. As shown, a series of two implants (18' and 18") can be inserted into a damaged bone to prevent further damage during healing.

In addition, the implant body may be used alone to join cartilagenous tissues together, such as in the repair of articular cartilage or the meniscus.

Figure 10A:
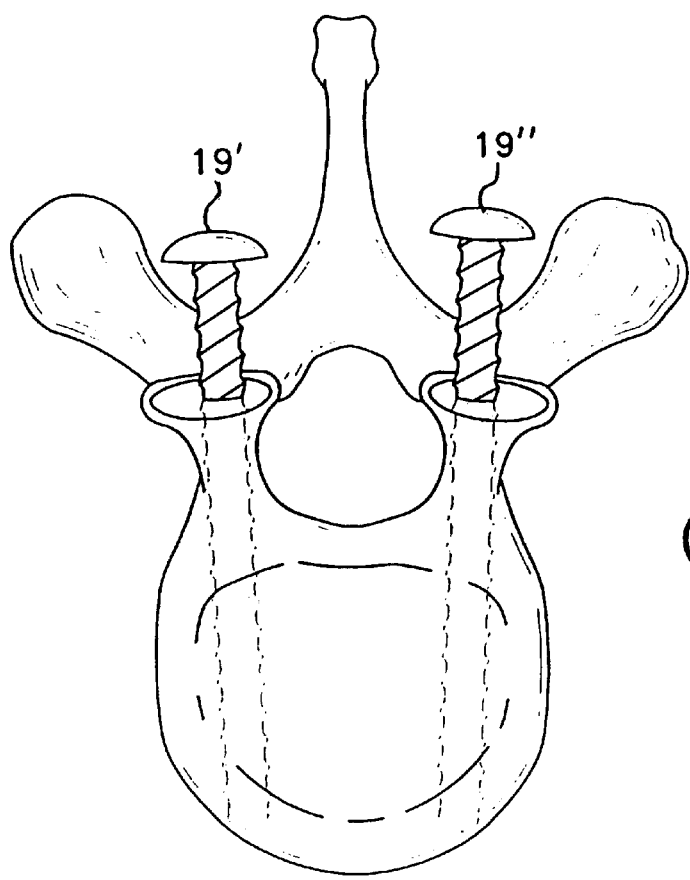
FIG. 10a is a graphical representation of two surgical screws deployed within a hard tissue.
Figure 10B:
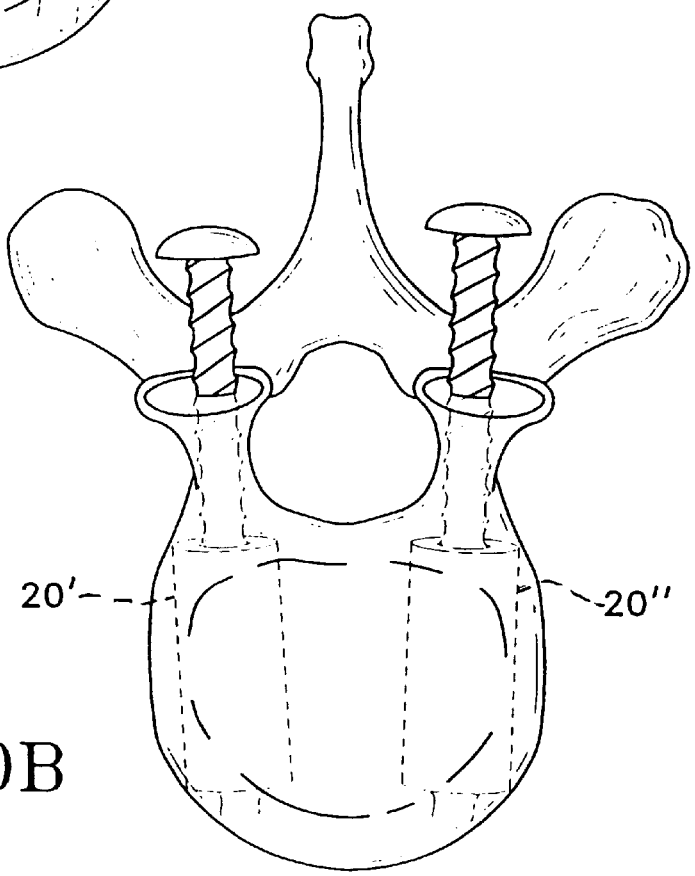
FIG. 10b is the same graphical representation showing the use of a representative embodiment of the implant of the present invention as a platform for the surgical screws.
Figure 11A:
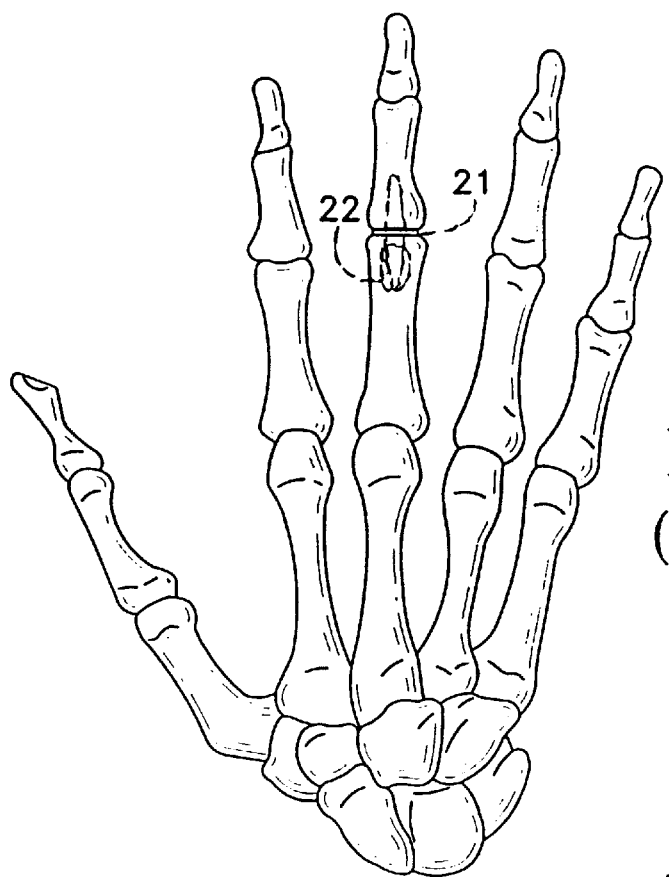
FIG. 11a is a graphical representation of a hand bone depicting an artificial joint and a bone defect.
Figure 11B:
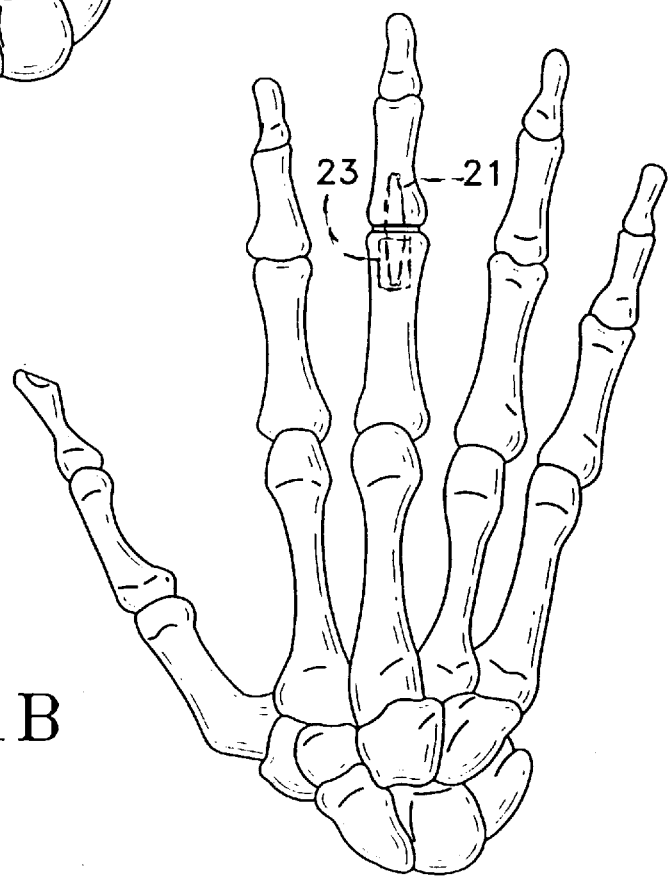
FIG. 11b is the same graphical representation showing the use of a representative embodiment of the implant of the present invention as a platform for the artificial joint.

The implant of the present invention may also be used to enhance the mechanical integrity and thus the load bearing capacity of a hard tissue by serving as a platform for attachment of a surgical device such as a screw, rod or pin. See FIGS. 10a and b, and 11a and b and refer to Example 8 for a further explanation. As shown in FIG. 10a, surgical screws (19' and 19") are commonly used in bone repair. FIG. 10b shows the use of a series of implants (20' and 20") which are used to facilitate fixation of the screws. FIG. 11a shows the use of an artificial joint (21), one end of which is inserted into a bone with a boney defect (22). As shown in FIG. 11b, an implant (23) can be used to enhance the structural integrity of the bone at the location of the boney defect.

In these applications, the implant may contain a cavity which is adapted to receive the surgical device. The cavity can be formed either by using an appropriately shaped mold to form the implant body, or the implant body can be sculpted after formation.

Shaping the Polymer Matrix

In a preferred embodiment of the present invention, the polymer matrix is shaped by extruding the reaction mixture containing the matrix material and any other optionally included components through a specially designed "mold die." The mold die functions by changing the cross-sectional orientation of the polymeric material during the extrusion process, which provides for different shrinkage characteristics across the cross-section of the matrix during drying. Accordingly, in order to retain this change in orientation throughout the entire length of the mold, the reaction mixture should be sufficiently viscous prior to extrusion to maintain its shape during and after extrusion. This generally necessitates that the reaction mixture is somewhat gelatinous, i.e. it has some of the physical properties of a quasi-solid.

Figure 12:
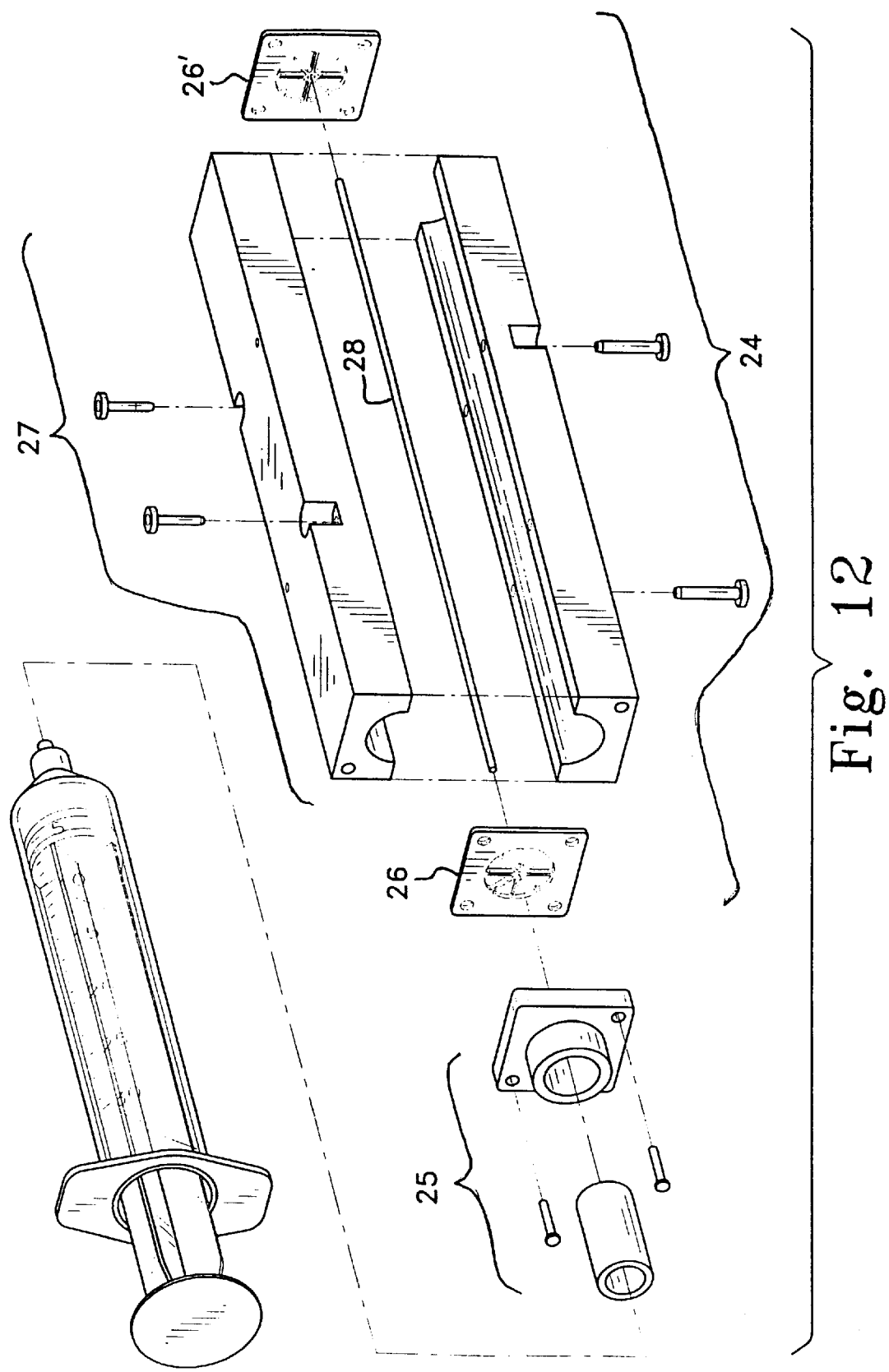
FIG. 12 is a perspective view of a representative embodiment of an apparatus (i.e. a polymer body shaping device), before assembly, which is used to make a polymer body according to the present invention.

A representative embodiment of an apparatus (24) according to the present invention is shown in FIG. 12. Also depicted in FIG. 12 is a standard syringe which can be used to load the reaction mixture into the mold. The apparatus, excluding the syringe, is also referred to herein as a "polymer body shaping device" or simply a "shaping device."

As shown in FIG. 12, a two-piece syringe adapter (25) can be used along with the shaping device (24), and may also be useful in holding the mold die (26) in place next to the two-piece mold (27). For convenience, a second mold die (26') can be used to hold a mandrel (28) in place. The mandrel is used to form a polymer body with a channel running through its length as described above and depicted in FIG. 1.

Figure 14A:
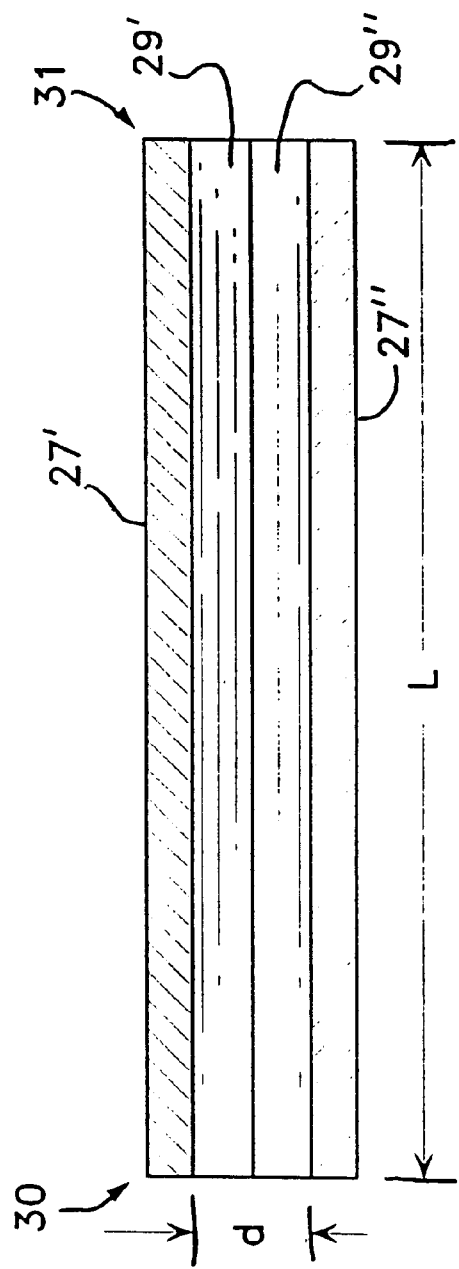
FIG. 14a is a perspective cross-section view of the mold of FIG. 13 without the polymer mixture/matrix therein.
Figure 14B:
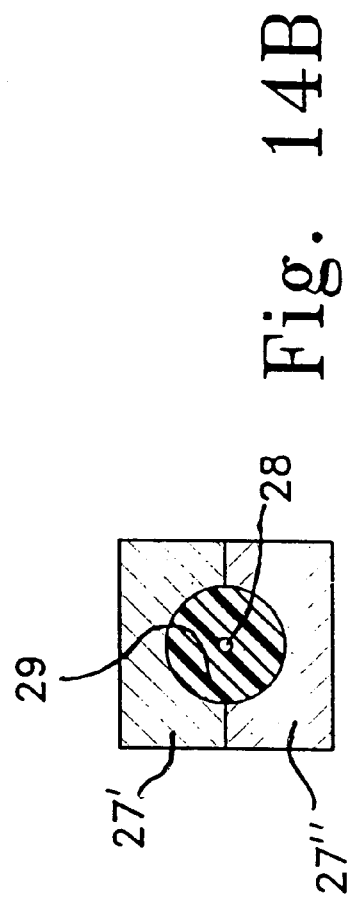
FIG. 14b is a cross-section view of the same mold showing the polymer mixture/matrix in the cavity defined by the mold.

As depicted in FIG. 14a in the absence of the polymer mixture/matrix, the inner walls (29' and 29") of the two pieces of the mold (27' and 27") join together to form one continuous inner surface which defines an elongated cavity into which the polymer mixture is extruded. The mold has a length, "1," and an inner diameter, "d," and the cavity extends along the longitudinal axis of the mold between the proximal end (30) and distal end (31) of the mold. Then, as shown in FIG. 14b after extrusion of the polymer mixture into the mold, the polymer mixture fills the cavity and surrounds the mandrel (28).

In a preferred embodiment, the mold defines an elongated cylindrically-shaped cavity and has a length and inner diameter which are sufficient to produce a polymer body with the desired length and width, respectively. For making implant bodies for tissue repair, typically the length of the mold is between about 75 mm and about 300 mm, more preferably about 150 mm, and the diameter of the cavity is preferably between about 9 and about 14.5 mm.

Figure 13:
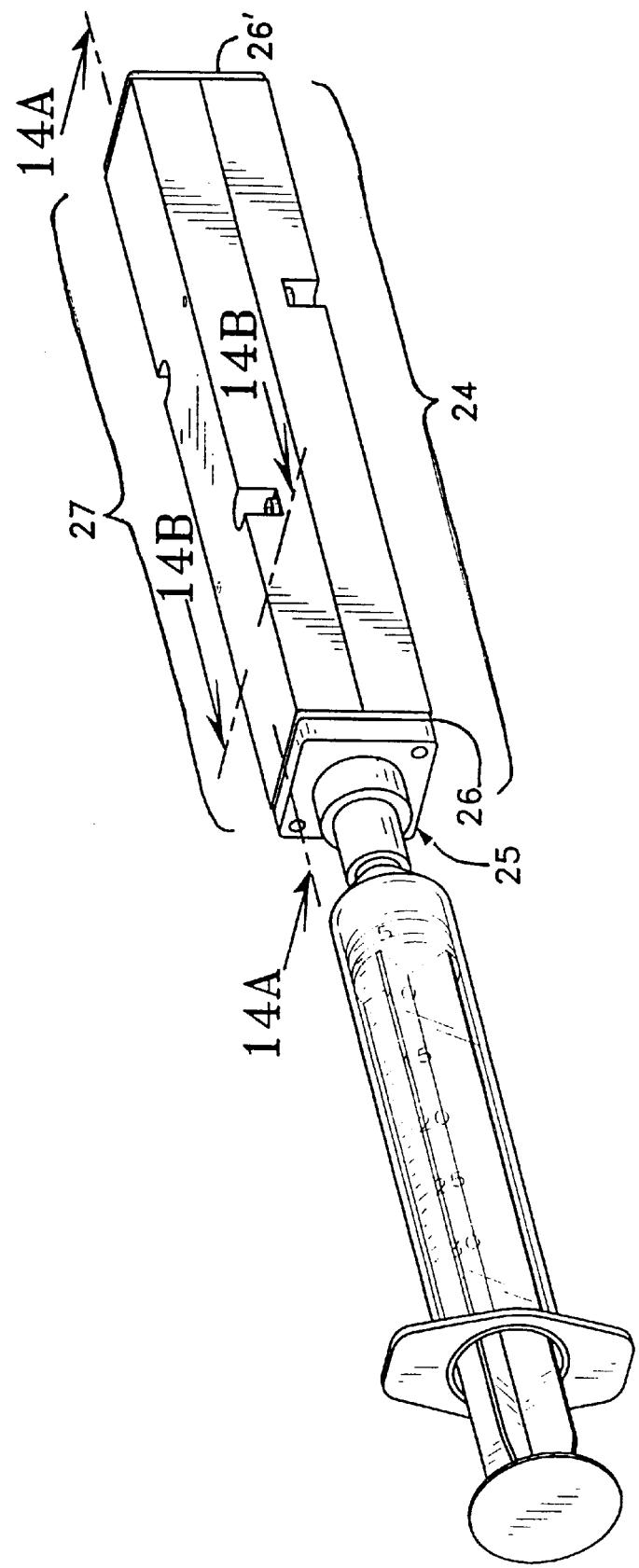
FIG. 13 is a perspective view of the apparatus (and syringe) depicted in FIG. 12 after assembly.
Figure 15A:
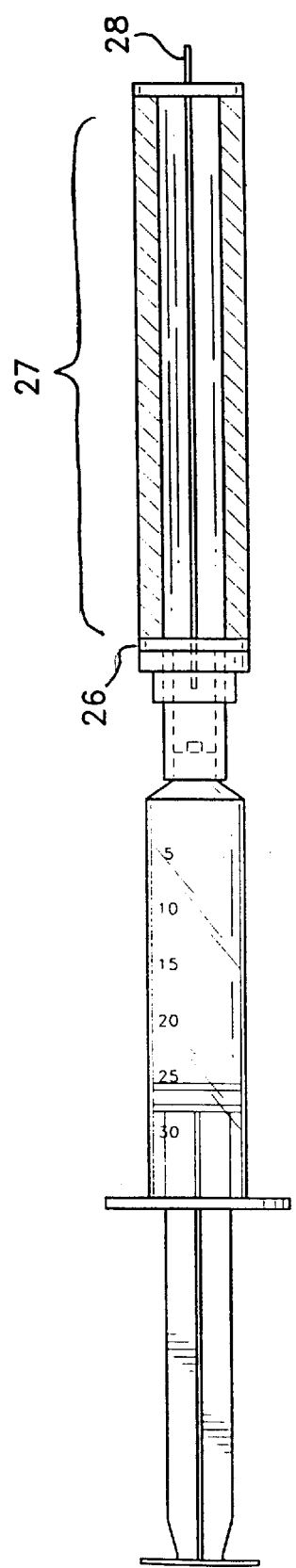
Figure 15B:
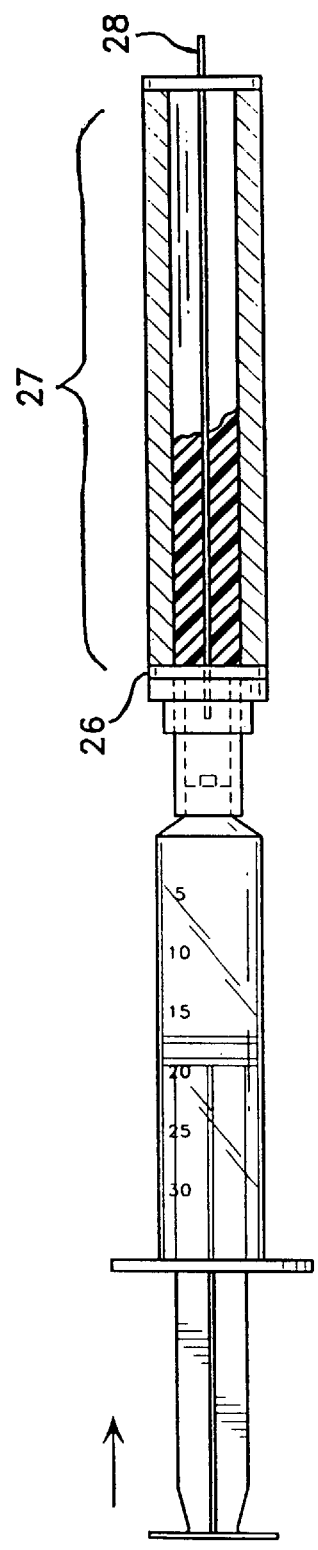
Figure 15C:
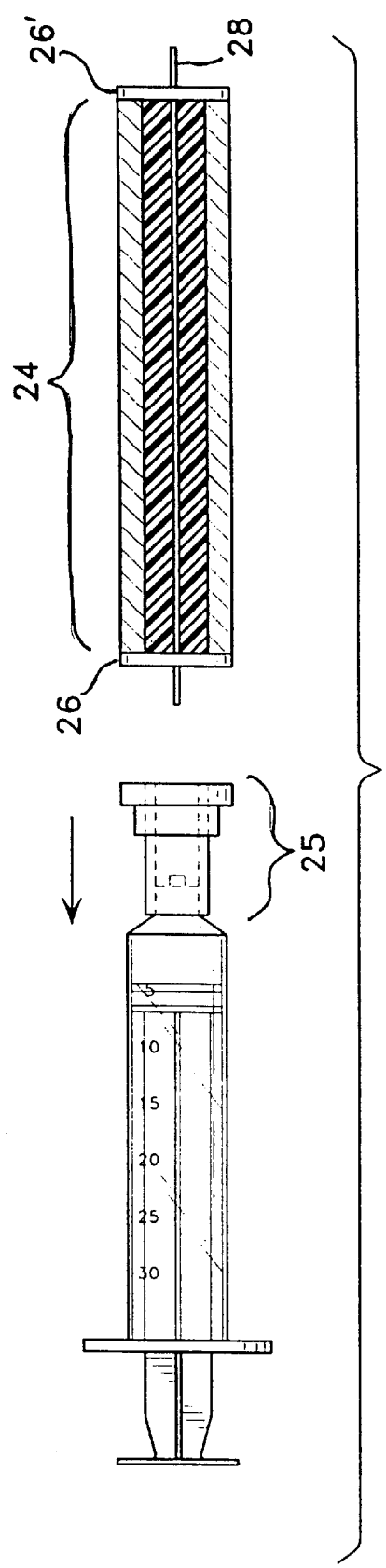
Figure 15D:
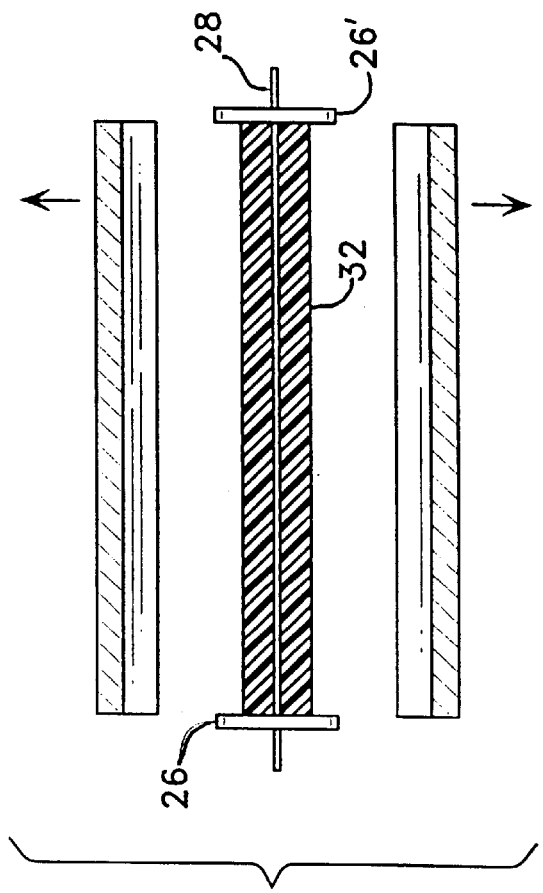
Figure 15F:
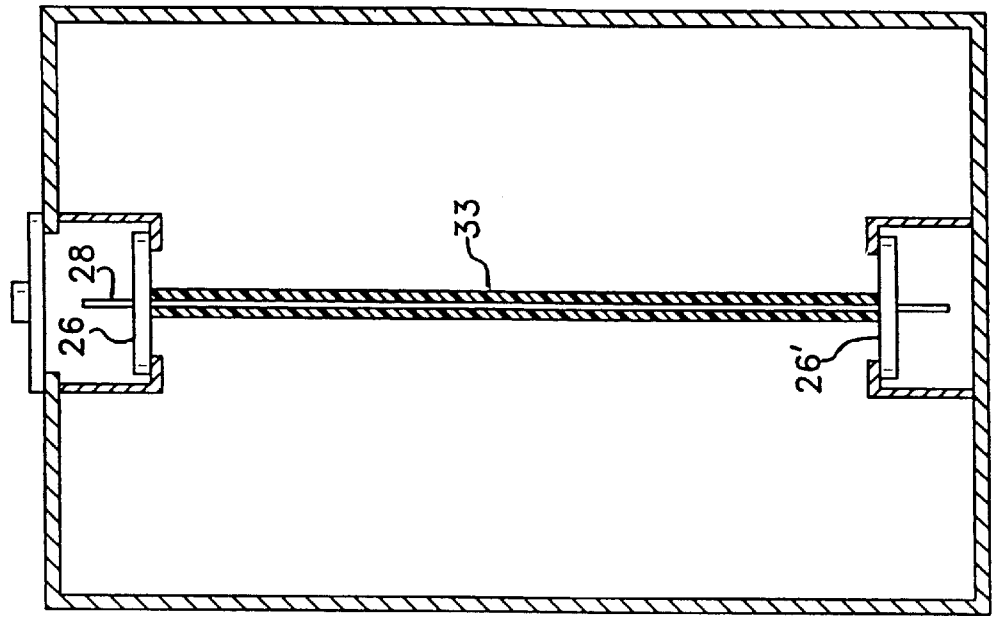
Figure 15E:
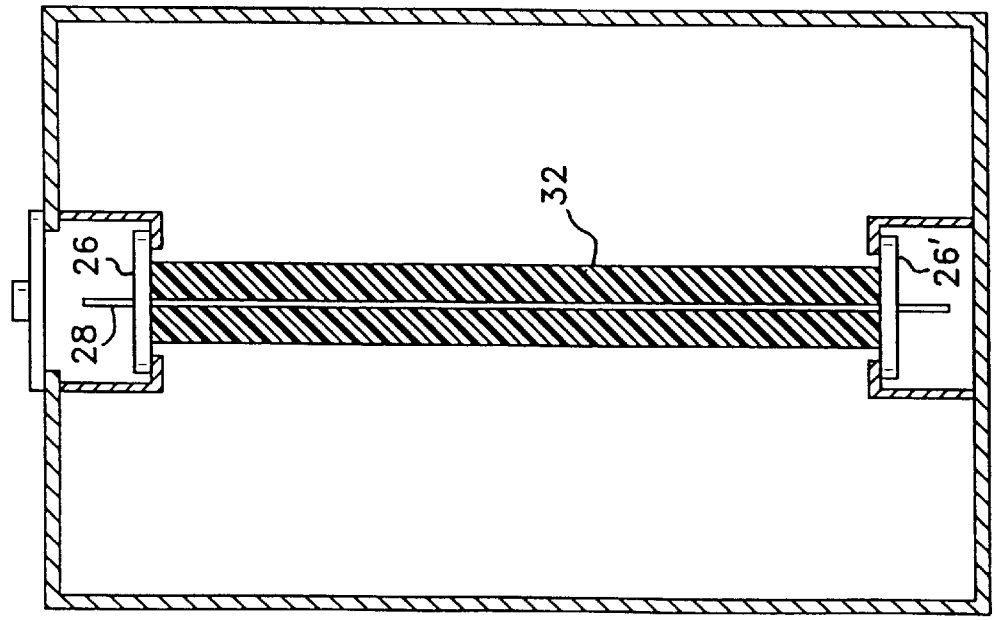

FIGS. 15a–h show how the shaping device depicted in FIGS. 12 and 13 can be used to form uniformly shaped polymer bodies of different lengths. FIG. 15a shows a cross-section of the shaping device (and a side view of the syringe containing the reaction mixture) before extrusion through the mold die (26) into the mold (27). FIG. 15b shows the same view after partial extrusion of the reaction mixture into the mold (27). FIG. 15c shows the shaping device after extrusion has been completed and the syringe and syringe adapter (25) have been disconnected from the shaping device (24). FIG. 15d shows the same shaping device after the two-piece mold has been disassembled to expose the polymer matrix (32). At this stage, the polymer matrix is still "wet," but is capable of retaining its shape during further processing. As shown in FIG. 15d, the two mold dies (26 and 26') can be kept at either end of the elongated polymer matrix to hold the mandrel (28) in place during drying. FIGS. 15e and f show the polymer matrix in a drying oven before (15e) and after (15f) drying the polymer matrix. In a preferred embodiment, the polymer matrix is hung vertically in the drying oven, and allowed to dry at a sufficient temperature and a sufficient length of time to drive water from the matrix without harming the biocompatible polymer. For collagen, this temperature is generally between 22° C. and 35° C., and for polymer matrix having a diameter of 14.4 mm, a drying time of 18–36 hours is preferred to achieve a final moisture content of 2–3% and a final diameter of about 3.5 mm.

FIG. 15g shows removal of the mold dies (26 and 26') and the mandrel (28) from the uniformly shaped polymer body (33). Finally, FIG. 15h shows the polymer body containing a central cavity (34) and a diameter, "d," being cut into desired lengths, "1."

Figure 16D:
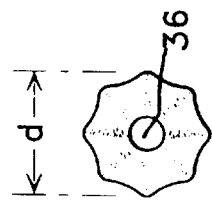
FIGS. 16a–d depict a cross-section of the relationship between the shape and appearance of a polymer body and the corresponding shape and appearance of the mold die through which the polymer material is extruded during formation of the polymer body.
Figure 16B:
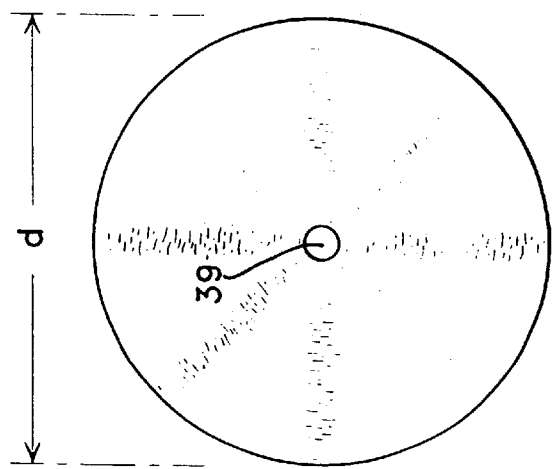
Figure 16C:
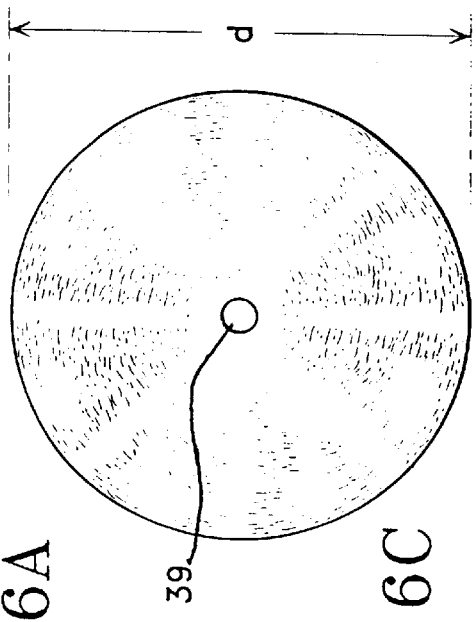
Figure 16A:
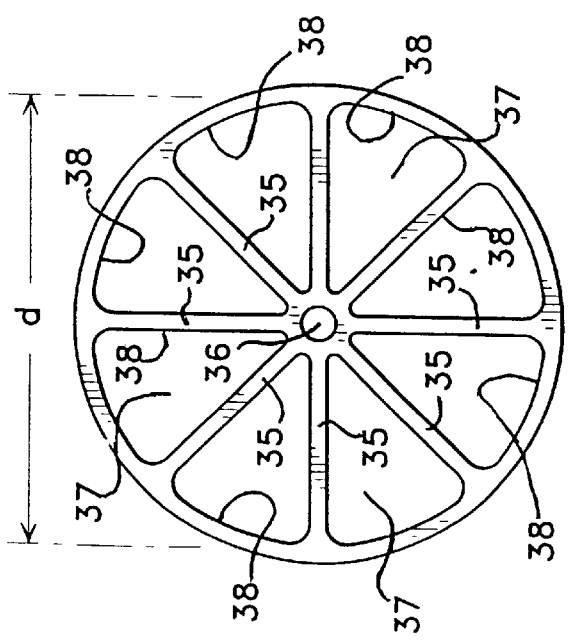
Figure 18A:
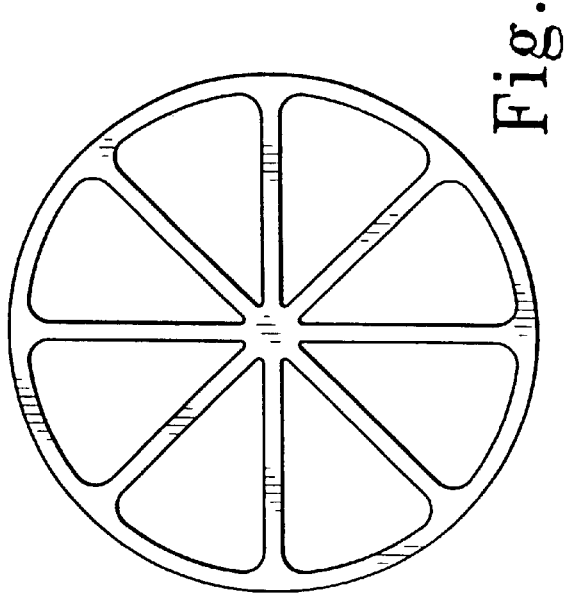
FIGS. 17 to 21 depict cross-sections of various alternate embodiments of mold dies (FIGS. 17a, 18a, 19a, 20a and 21a) and the corresponding dried polymer bodies (FIGS. 17b, 18b, 19b, 20b and 21b, respectively.)
Figure 18B:
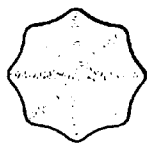
Figure 17A:
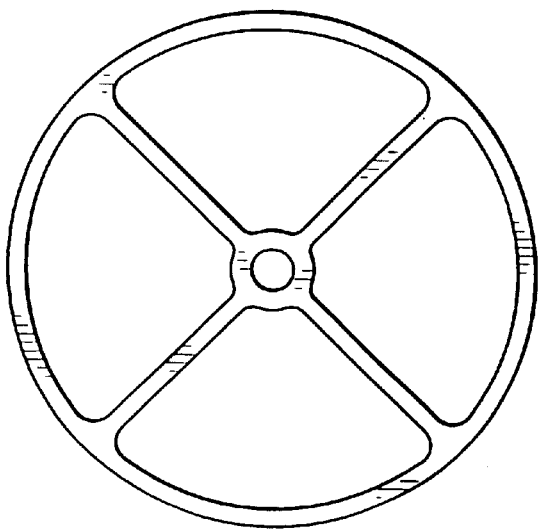
Figure 17B:
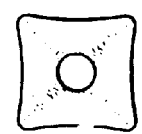
Figure 20A:
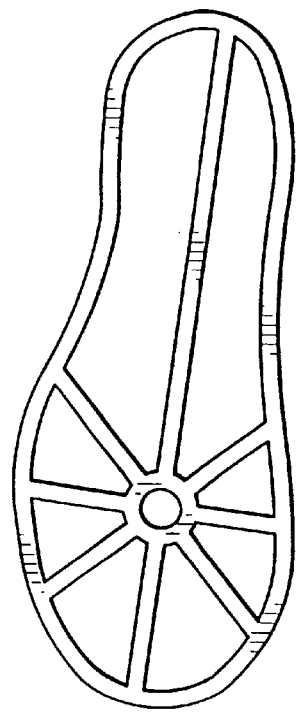
Figure 20B:
Figure 19A:
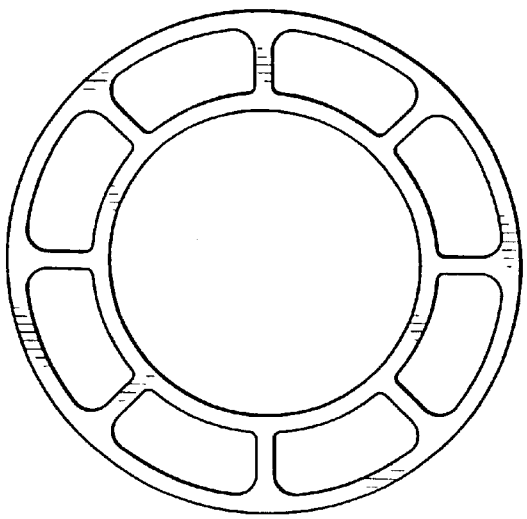
Figure 19B:
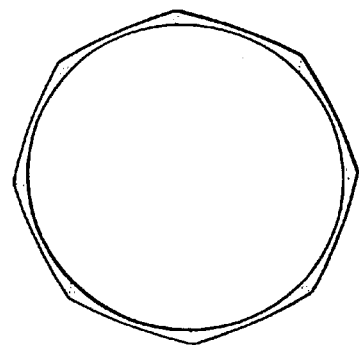
Figure 21B:
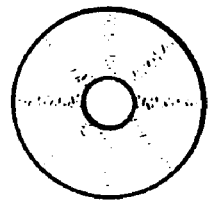
Figure 21A:
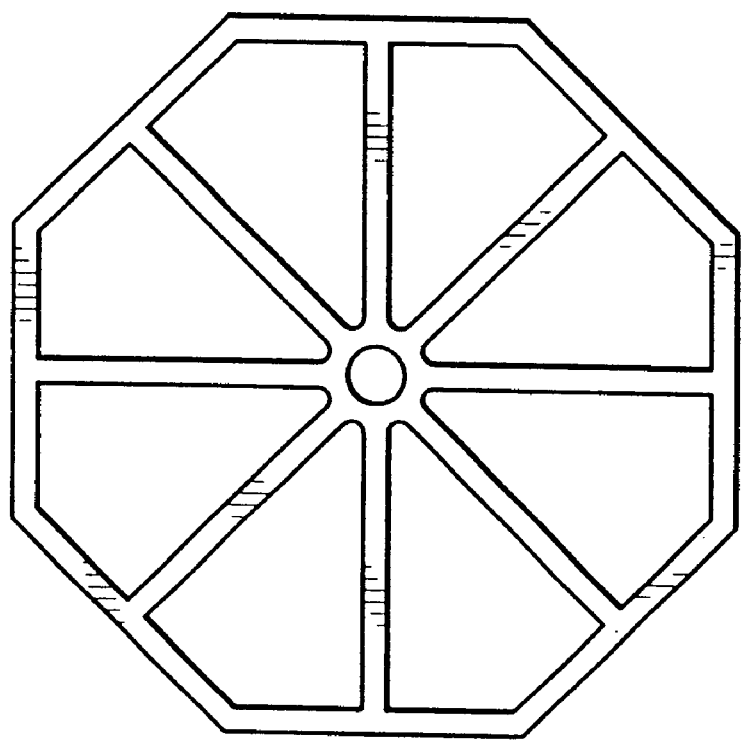

FIGS. 16a–d depict a cross-section of the relationship between the shape and appearance of a polymer body and the corresponding shape and appearance of the mold die through which the polymer material is extruded during formation of the polymer body. This relationship dictates the drying characteristics of the polymer matrix, which in turn dictates both the shape and rehydration characteristics of the polymer body. A cross-section of a preferred embodiment of a mold die is shown in FIG. 16a. As shown therein, the preferred mold die design is that of a "spiderwheel" having a plurality of angularly spaced ribs (35) which fan out radially from the axis of the spiderwheel (36) and form a plurality of apertures (37) shaped like "pieces of a pie" in the mold die through which the polymer material can be extruded. Also shown is a central core in the mold die which runs along the axis (36), and which could be occupied by a mandrel as described above and shown in FIGS. 15a–f. It is hypothesized that during extrusion, the polymer molecules come in contact with the inner surfaces (38) of these apertures (37) and become oriented in a direction which is parallel to the direction of extrusion, i.e. along the length of the mold.

FIG. 16b shows the appearance of the polymer matrix (i.e. the undried polymer body) under normal fluorescent light after it has been extruded through the mold die into the mold. As shown, the areas corresponding to the location of the ribs (where the polymer molecules came in contact with the inner surfaces of the apertures) appear darker. Also shown is that, even though the polymer matrix is extruded through eight different apertures which effectively splits the polymer matrix into eight separate streams as it passes through the mold die, the polymer matrix is sufficiently gelatinous for these separate streams to rejoin into one continuous matrix after extrusion. In addition, the pattern of reflected light which is shown in FIG. 16b would be expected to be consistent throughout the length of the mold die. If it was not, the length of the mold die can be shortened, the viscosity of the polymer matrix can be increased, or the flow rate of extrusion can be slowed, or a combination of these can be employed, to ensure uniformity of the shape and physical properties of the dried polymer body.

FIG. 16c shows the appearance of the polymer matrix under polarized light. Again, it can be seen that the areas corresponding to the location of the ribs have a different appearance that the areas in-between the ribs which suggests that the polymer molecules in these areas may be oriented differently. FIG. 16c shows the dried polymer body which, as shown, has shrunk in diameter to about one fifth its size when wet (FIGS. 16b and c), while the diameter of the central core (39) has remained the same. Also shown in FIG. 16d is the pattern of shrinkage of the polymer body using this type of mold die. As shown, shrinkage is greater in-between the areas where the polymer came into contact with the ribs of the mold die, resulting in a "star shaped" polymer body. These areas of greatest shrinkage also provide for efficient rehydration and associated swelling of the polymer body once it is reexposed to an aqueous environment. It is also important to note that, using a slower flow rate through the mold die, the star is less pronounced and the same mold die can be used to produce an octagonal shape. When the flow rate is increased, the shape of the star becomes more pronounced.

The mold die can have any shape, size and design which is necessary to achieve the desired size and swellability, and can be easily designed according to the principles described above for the spiderwheel design. However, in a preferred embodiment, the mold die has an essentially central axis with at least three ribs extending radially outward therefrom which form at least three separate apertures through which the polymer material is extruded. It may also be desirable to use a mold die with two or more axes, ribs which are not straight, apertures which are unequal in size, etc. Examples of different mold dies, each having a distinctive pattern, and the corresponding polymer bodies which are formed by extrusion through these mold dies are shown in FIGS. 17–21.

The following examples are put forth so as to provide those of ordinary skill in the art with a complete disclosure and description of how to make the preferred embodiments of the conjugates, compositions, and devices, and are not intended to limit the scope of what the inventors regard as their invention.

EXAMPLE 1

Preparation of Collagen-Based Bone Suture Anchor

A solution of glutaraldehyde (in PBS pH 7.4) was prepared with a final aldehyde concentration of 1550 ppm. A 30 cc syringe was filled with 9.3 grams of the glutaraldehyde solution. A second 30 cc syringe was filled with 20 grams of fibrillar collagen at 70 mg/ml. (Collagen Corporation, Palo Alto, Calif.).

The syringe containing the collagen suspension was connected to the syringe containing the glutaraldehyde solution using a syringe connector. The glutaraldehyde and collagen were mixed using syringe-t syringe mixing for 20–40 passes of material between the syringes.

The collagen/glutaraldehyde reaction mixture was extruded into two separate cylindrical molds each having a 13 mm outside diameter and a mandrel running through the center, and incubated at 37° C. for one hour to allow complete crosslinking to be achieved between the collagen and the glutaraldehyde. The resulting implant body was removed from the mold and soaked in deionized water overnight at room temperature.

The preformed body was dried for two days at room temperature, then placed in an oven at 37° C. for about 24 hours to complete the drying process, then terminally sterilized using gamma irradiation.

EXAMPLE 2

Preparation of Collagen-Based Bone Suture Anchor Containing Ceramic Particles

A solution of glutaraldehyde in PBS pH 7.4 was prepared with a final aldehyde concentration of 1550 ppm. A 30 cc syringe was filled with a mixture of 20 ml fibrillar collagen at 70 mg/ml with 1.4 grams tricalcium phosphate (TCP) (50% wt./wt.).

The syringe containing the collagen/TCP mixture was connected to the syringe containing the glutaraldehyde solution using a syringe connector. The glutaraldehyde and collagen/TCP mixture were mixed using syringe-to-syringe mixing for 20–40 passes of material between the syringes.

The collagen/TCP/glutaraldehyde reaction mixture was extruded into two separate cylindrical molds, each having an 11 mm outside diameter and a mandrel running through the center, and incubated at 37° C. for one hour to allow complete crosslinking to be achieved between the collagen and the glutaraldehyde. The resulting preformed body was removed from the mold and soaked in deionized water overnight at room temperature, then dried in an oven at 37° C. for 18 hours, then terminally sterilized using gamma irradiation.

EXAMPLE 3

Hydration of Collagen-Based Bone Suture Anchors

The diameter of a dehydrated glutaraldehyde-crosslinked collagen implant body, prepared as described in Example 1 (before sterilization), was measured using digital calipers. Each implant body was placed in a 20 cc vial with 15–20 ml of phosphate buffered saline (PBS, pH 7.35), then stored at 37° C.

After various time points up to 72 hours, the implant body was removed from the vial, rinsed and blotted to remove excess water. The dimensions of the implant body were measured, then the implant body was returned to the vial for further hydration. The results are given below in Table 1. (It should be noted that expansion during the use will be limited by the diameter of the hole and the quality of the bone.)

TABLE 1

Hydration Results

| Time | % Weight Gain | % Length Gain | % Diameter Gain |
|---|---|---|---|
| 1 hr | 81 | 0 | 17 |
| 3 | 130 | 1 | 32 |
| 6 | 149 | 2 | 36 |
| 24 | 184 | 3 | 40 |
| 48 | 187 | 3 | 41 |
| 72 | 179 | 3 | 46 |

EXAMPLE 4

Mechanical Testing of Collagen-Based Bone Suture Anchors in Sawbones

The mechanical strength of glutaraldehyde-crosslinked collagen bone anchors (collagen bone anchors), prepared as described in Example 1, and glutaraldehyde-crosslinked collagen bone anchors containing ceramic particles (collagen—ceramic bone anchors), prepared as described in Example 2, was measured in Sawbones™, a polymeric foam bone model (manufactured by Pacific Research Laboratories, Vashon, Wash.). A commercially available bone suture anchor, the Innovasive 3.5™, was used as a control.

The bone anchors were placed in 3.5 mm diameter, 13 mm deep depressions in the Sawbones and allowed to rehydrate in 37° C. PBS until maximum strength was achieved. The anchors were then pulled perpendicular to the Sawbones surface at a rate of 100 millimeters per minute using an Instron Model 4202. Results of pull-out testing are presented in Table 2, below.

TABLE 2

Holding Strength

| Anchor Type | Holding Strength (N) |
|---|---|
| Collagen | 162 |
| Collagen - ceramic | 159 |
| 3.5 ROC ™ | 228 |

All three anchor types tested demonstrated holding strengths greater than the minimum average breaking strength of a double-stranded #2 suture containing one knot (~124 N).

EXAMPLE 5

Mechanical Testing of Collagen-Based Bone Suture Anchors in Cadaver Bone

The mechanical strength of glutaraldehyde-crosslinked collagen bone anchors (collagen bone anchors), prepared as described in Example 1, and glutaraldehyde-crosslinked collagen bone anchors containing ceramic particles (collagen—ceramic bone anchors), prepared as described in Example 2, was measured in the greater tuberosity of the humeral head of cadaver bones. This site was chosen as it is the specific site used in rotator cuff repair. A commercially available bone suture anchor, the Innovasive 3.5 ROC™, was used as a control.

The bone anchors were hydrated in situ for at least one hour in physiological solution at 37° C., then pulled perpendicular to the bone surface at a rate of 305 millimeters per minute using an Instron Model 8511. For some of the samples, stainless steel wire was used in place of the Dacron #2 suture in order to permit measurement of the ultimate pull-out strength of the anchor.

The ultimate pull-out strength of the collagen bone anchors (n=8) was measured to be 160±47 N. The ROC™ anchors (n=3) failed at 119±32 N. In similar testing performed in cadaver glenoid rims (the site for capsular repair), the ultimate pull-out strength of the collagen bone anchors (n=6) was measured to be 170±57 N.

EXAMPLE 6

Soft Tissue to Hard Tissue Repair

The implant disclosed may be used alone or in multiples to reattach avulsed soft tissue to hard tissue, for example, in repair of the rotator cuff of the shoulder. In this example, a cavity is created in the trough between the humeral head and the greater tuberosity of the humerus. The implant which includes an implant body, a load-distributing device, and suture (hereinafter referred to as "bone anchor") as depicted in FIG. 1 is introduced into a cavity. This may be accomplished by hand pressure or by using an instrument consisting of a sleeve into which the bone anchor is placed and a plunger which forces the anchor into the cavity. The bone anchor is placed into the cavity so that the anchor is countersunk below the surface of the humeral trough with the free ends of the suture protruding out of the cavity. The free ends of the suture are then passed through the avulsed tendon and tied on the superior surface. One or more bone anchors may be used to repair the rotator cuff, these anchors being spaced a suitable distance apart in the humeral trough. With time, the implant body is resorbed and replaced by native tissue. The load-distributing member and suture may or may not resorb depending upon the material employed in their construction. In any case, the cavity created to receive the anchor is filled by native tissue, which may be expected to enhance the soft tissue to hard tissue repair.

Another example of soft tissue to hard tissue repair is in reattachment of the glenoid labrum of the shoulder to the scapula ("Bankart Repair"). In this example, a cavity is created in the periphery of the glenoid rim of the scapula. The implant body, load-distributing device, and suture (hereinafter referred to as "bone anchor") is introduced into the cavity. This may be accomplished by hand pressure or by using an instrument consisting of a sleeve into which the bone anchor is placed and a plunger which forces the anchor into the cavity. The bone anchor is placed into the cavity so that the anchor is countersunk below the surface of the glenoid rim with the free ends of the suture protruding out of the cavity. The free ends of the suture are then passed through the avulsed glenoid labrum and tied on the surface away from the scapula. One or more bone anchors may be used to repair the glenoid labrum, these anchors being spaced a suitable distance apart around the periphery of the glenoid rim. With time, the implant body is resorbed and replaced by native tissue. The load-distributing member and suture may or may not resorb depending upon the material employed in their construction. In any case, the cavity created to receive the anchor is filled by native tissue, which may be expected to enhance the soft tissue to hard tissue repair.

Another example of soft tissue to hard tissue repair is in reattachment of the patella tendon (ligamentum patellae) to the tibial tubercle. In this example, a cavity is created in the tibial tubercle. The implant body, load-distributing device, and suture (hereinafter referred to as "bone anchor") is introduced into the cavity. This may be accomplished by hand pressure or by using an instrument consisting of a sleeve into which the bone anchor is placed and a plunger which forces the anchor into the cavity. The bone anchor is placed into the cavity so that the anchor is countersunk below the surface of the tibia with the free ends of the suture protruding out of the cavity. The free ends of the suture are then passed through the avulsed patella tendon and tied on the superior surface. One or more bone anchors may be used to repair the patella tendon, these anchors being spaced a suitable distance apart laterally across the tibia. With time, the implant body is resorbed and replaced by native tissue. The load-distributing member and suture may or may not resorb depending upon the material employed in their construction. In any case, the cavity created to receive the anchor is filled by native tissue, which may be expected to enhance the soft tissue to hard tissue repair.

EXAMPLE 7

Attachment of Two Hard Tissues using the Implant (Implant Body)

As depicted in FIGS. 9a and 9b, the implant may be used to attach two hard tissues together by means of mechanical forces alone. Although two implants were used in each of the applications depicted in FIGS. 9a and 9b, it is possible to use a single implant, or a series of three or more implants. In the example of osteochondritis dessicans, a free osteochondral fragment may be reattached to the articular surface of the femur using one or more of the implants in a manner similar to a surgical pin (FIG. 9b). The fragment is aligned with the defect in the articular surface and one or more of the implants are driven through the fragment into the subchondral bone. Once in place, the apparatus swells and achieves an interference fit in both the fragment and the underlying bone, maintaining the two in close apposition and facilitating healing of the osteochondral fragment to bone. With time, the implant resorbs and is replaced by native tissue, leaving no residual material to interfere the normal remodeling process of bone nor to act as a stress riser that could provide an initiation site for a new fracture. Likewise, any bone chip may be reattached to the bony site from which it came using the same method described.

In another example as depicted in FIG. 9a, the implant may be used to join two ends of a fractured small bone together to enable fracture repair. In the case of metacarpal (finger bone) fracture, the two ends of the bone can be aligned and one or more of the apparatus driven lengthwise through the intermedullary space. Once in place, the apparatus swells and achieves an interference fit in both fragments of bone, maintaining the two in close apposition and facilitating healing of the two bone fragments. With time, the implant resorbs and is replaced by native tissue, leaving no residual material to interfere the normal remodeling process of bone nor act as a stress riser that could provide an initiation site for a new fracture.

EXAMPLE 8

Using the Implant (Implant Body) as a Platform for the Attachment of a Surgical Device It is often difficult to achieve adequate holding strength of a screw in poor quality bone. One example is the case of implanting screws in the vertebral pedicles of osteoporotic women for attachment of plates to effect spinal fusion as depicted in FIG. 10a. As shown in FIG. 10b, the implant facilitates fixation of the screw to the vertebral body by acting as a sleeve between screw and bone, filling the gaps in the bone and providing a more uniform surface for the screw threads to engage.

As such, the implant provides improved immediate holding strength of the screw into the vertebrae. With time, the apparatus is resorbed and replaced by native tissue which fills the space up to the threads of the screw.

Similarly, as depicted in FIGS. 11a and b, the implant may be used in revision synthetic implant surgery to fill gaps in bone caused by osteolysis prior to insertion of a new synthetic implant into the site. In this example, the implant may be inserted into the intermedullary canal of the metacarpal after removal of the failed synthetic total finger joint replacement to fill gaps caused by osteolysis (FIG. 11a). A new total finger joint may then be inserted with the stem of the joint being driven into a cavity in the center of the insert as depicted in FIG. 11b. In this way, the implant provides a platform for the total finger joint in the bone, enhancing its immediate stability. With time, the implant is resorbed and replaced by native tissue which fills up the space up to the surface of the synthetic implant stem.

EXAMPLE 9

Mechanical Testing of Collagen-Based Pins in Sawbones

The shear strength of glutaraldehyde-crosslinked fibrillar collagen pins was measured in Sawbones. Pins were placed into 2.6 mm diameter holes in adjoining Sawbones and allowed to rehydrate in 37° PBS for three days. The Sawbones were pulled apart at a rate of 50 mm/minute using an Instron Model 4202. The orientation of the pins in the Sawbones was such that the pins were subjected primarily to shear forces. The strength of the pins was determined to be approximately 6 MPa.

EXAMPLE 10

Tendon to Bone Healing Using an Ovine Patellar Tendon Model

The biomechanical and histological properties of patellar tendons reattached using metallic and collagen implants was examined in a sheep model. Sixteen adult sheep (45–50 kg) were used. Ten animals had unilateral patellar tendon reconstructions using a metallic suture anchor (Mitek Rotator Cuff Anchors, n=2) or one of four variations of a collagen implant (CBA, n=2). Two implants were used to repair each tendon. The CBAs were composed of either dehydrated glutaraldehyde-cross linked fibrillar collagen or dehydrated glutaraldehyde-cross linked fibrillar collagen with tricalcium phosphate, and were prepared as described in Examples 1 and 2, respectively. All CBAs included a load distributing device made of polymethyl methacrylate (PMMA). The CBAs were gamma irradiated (2.5 Mrad) or aseptically prepared. The patellar tendon was elevated from its tibial insertion site and repaired by the insertion of two implants into the tibia and then attached with a #2 braided polyester suture using a modified whip stitch. Immediately following surgery the animals were bandaged in full extension using a modified bulky soft bandage. The bandages were removed after 21 days and animals were sacrificed six weeks post-operatively. The right and left hind limbs were x-rayed, mechanically tested, and histologically processed.

The remaining six sheep had bilateral patellar tendon reconstructions using either the Mitek or CBA anchors. These animals were sacrificed immediately following surgery and tested.

Mechanical testing was performed using a specially designed jig which mounted the patella-patellar tendon-tibia (P-PT-T) complex in an MTS 858 Testing Machine, and the operated or non-operated limbs were subjected to a load. The peak load to dislodge the patellar tendon from the tibia was determined. Histology was performed on the healing tendons and a portion of the proximal tibia which contained the implants. Four non-operated control tendons were also histologically examined.

Results of Time Zero Testing: The peak load of the time zero repairs using the CBA devices was equivalent to the repairs using the Mitek devices (see Table 3.)

Results of 6 Week Testing: Mechanical testing of the P-PT-T complexes at 6 weeks revealed a significant increase in peak load compared to the time zero testing. As shown in Table 3, the repaired samples remained significantly weaker than the non-operated (control) patellar tendons. No significant difference in peak load was found between the Mitek and CBA repairs.

Histologically, the healing patellar tendon-bone interface at 6 weeks presented dense connective tissue with plump fibroblastic cells. Modest CBA degradation and mild inflammatory cell responses were observed. New bone tissue was observed growing adjacent to the CBA as well as the metallic Mitek anchors. New bone tissue was also observed to be forming within the degrading CBA matrix.

TABLE 3

| Group | Time (wks) | Peak Load, N (mean ± sd) |
|---|---|---|
| Mitek | 0 | 246 ± 19 |
| CBA | 0 | 274 ± 21 |
| Mitek | 6 | 1119 ± 12 |
| CBA | 6 | 1208 ± 490 |
| Control | 6 | 2481 ± 408 |

EXAMPLE 11

Biocompatibility and Degradation of Collagen Bone Anchors in a Rabbit Model

Introduction

Bone anchors, which facilitate reattachment of soft tissue to bone, are currently made from metal, nondegradable plastics, and synthetic bioabsorbable polymers. The ideal bone anchor would provide initial stabilization of soft tissue, be easily deployed arthroscopically, be degraded over time, and be eventually replaced by normal bone. Bioabsorbable collagen-based implants have been used successfully for bone grafting (Cornell CN, et al., *J Orthop Trauma* 5(1):1–8, 1991) and soft tissue augmentation (Keefe J. et al., *Clin Mater* 9:155–162, 1992). The objective of this study was to evaluate the biocompatibility and degradation of two collagen bone anchor formulations in a rabbit model.

Materials and Methods

The implant devices used in this study were two-part devices: an implant body and a load-distributing device through which a suture could be threaded. See FIG. 1. The implant body consisted of dehydrated glutaraldehyde-crosslinked fibrillar collagen (FC) or glutaraldehyde-crosslinked fibrillar collagen with $\beta$-tricalcium phosphate ceramic particles (FC-TCP). FC is highly purified bovine dermal collagen which is >95% Type I and <5% Type III collagen. The button-shaped washer was made by yttria-partially stabilized zirconia (YTZP), and the suture was #2 braided polyester. The dried implant body hydrates in situ, swelling and locking the anchor into the predrilled bone hole. The washer provides suture slip capability (for arthroscopic knot tying) and distributes the suture load to the implant body. The assembled bone anchors were =3.4 mm diameter, =12 mm long. Both anchor formulations were sterilized by 2.5 Mrad of ionizing radiation.

Eighteen skeletally mature New Zealand White rabbits received an anchor in each lateral femoral condyle. The anchors were seated in 3.5 mm diameter, 14 mm deep holes so that the top of the anchor was 0–2 mm below the cortical surface. In this bilateral model, one implant was used for biomechanical pullout testing and the other was evaluated histologically. Nine rabbits received FC anchors and nine received FC-TCP anchors. Three rabbits per group were sacrificed after one, six, and twelve weeks.

Histological evaluations were performed by a veterinary pathologist on decalcified sections stained with hematoxylin and eosin. For pullout testing, the condyles were dissected free of all soft tissue and the sutures pulled at 100 mm/minute perpendicular to the bone surface until failure.

Results and Discussion

Histology: Progressive new bone formation and maturation over time was observed surrounding both anchor formulations. Mild to moderate mixed inflammatory cell infiltration was observed for both formulations; FC-TCP anchors also showed mild granulomatous inflammatory activity at later timepoints. Extensive degradation of the FC-TCP anchors was seen at six weeks, although both formulations showed comparable levels of degradation at 12 weeks. Osteoblast-like cells and new bone were observed within the collagen bodies by 12 weeks. Notable chondrogenic activity, mostly over the top of the anchor and down into the suture hole, was observed at 12 weeks for the FC formulation. For both formulations, a well-developed bony "cap" formed over the tops of anchors seated below the cortical bone layer; this cap was less established for anchors which protruded into that layer or above the surface.

Biomechanics: Pullout test results were consistent with histological findings. The pullout strengths at one week of 119N for FC and 115N for FC-TCP were not significantly different. The FC-TCP anchors showed 80% strength loss by six weeks, whereas the FC anchors took 12 weeks to show a similar drop. At later timepoints, the washer was able to pull through the degraded anchor body. One possible explanation for the increase in pullout strength from six to 12 weeks for the FC-TCP anchors may be bone ingrowth into the collagen body helping to lock the washer in place.

Conclusions

Both collagen bone anchor formulations were biocompatible in the cancellous bone environment. Histological evaluation and biomechanical tests showed that the FC-TCP formulation degraded faster than the FC formulation.

EXAMPLE 12

Forming a Fibrillar Collagen Polymer Body Using a Shaping Device

A solution of glutaraldehyde, in PBS pH 7.4, was prepared with a final aldehyde concentration of 1550 ppm. A 30 cc syringe was filled with 9.3 grams of the glutaraldehyde solution. A second syringe was filled with a fibrillar collagen suspension to a final concentration of 65 mg/ml.

The syringe containing the collagen suspension was connected to the syringe containing the glutaraldehyde solution using a syringe connector. The glutaraldehyde and collagen were mixed using syringe-to-syringe mixing for 20–40 passes of material between the syringes.

The collagen/glutaraldehyde reaction mixture was extruded into a shaping device having a cylindrical cavity and a teflon mandrel running longitudinally through the cavity as shown in FIGS. 15a–d. The shaping device also comprised a mold die as depicted in FIG. 16a. The extruded collagen matrix was allowed to incubate inside the shaping device for one hour at 37° C. to allow complete crosslinking. The resulting preformed collagen matrix was placed vertically in a drying oven and allowed to air dry under quiescent conditions at 15–25° C. for 18 –36 hours. The final tubular product had a water content of 2–3%, with a longitudinal shrinkage in a direction parallel to the central axis of the tube. The resulting dried tubular product had a final diameter of 3.5 mm, with a capability of expanding radially outward up to 14.5 mm upon rehydration.

Cross-sectional analysis of the collagen matrix, using polarized light and phase contrast viewing as illustrated in FIGS. 15c, revealed eight lines of different intensity, radiating from the central axis of the matrix. The eight lines were introduced into the gel by the spiderwheel-shaped mold die during extrusion. Since shrinkage rates during drying differed between the area around the extrusion lines and the undisturbed gel, the dried product of an implant body had a shape which, in cross-section, was generally of a star shape with eight points as shown in FIG. 16d.

Modifications of the above-described modes for carrying out the invention that are obvious to persons of skill in the field of polymer-based devices are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for securing a second tissue to a first tissue in a body of a mammalian subject, wherein the first and second tissues, comprising the steps of:

(a) inserting at least one implant into said hard tissues, such that each implant transverses both of said hard tissues, wherein the implant comprises a resorbable, swellable implant body comprising a dehydrated crosslinked biocompatible polymer; and (b) allowing the implant body to rehydrate in situ to anchor the implant into the first and second tissues.

2. The method of claim 1 wherein said implant body comprises collagen.

3. The method of claim 2 wherein said collagen is fibrillar collagen.

4. The method of claim 3 wherein said fibrillar collagen is type I collagen.

5. The method of claim 4 wherein said fibrillar collagen is human type I collagen.

6. The method of claim 2 wherein said collagen is crosslinked collagen.

7. The method of claim 6 wherein said crosslinked collagen is crosslinked with a functionally activated synthetic hydrophobic or hydrophilic polymer.

8. The method of claim 6 wherein said crosslinked collagen is crosslinked with an aldehyde-containing crosslinking agent.

9. The method of claim 8 wherein said aldehyde-containing crosslinking agent is glutaraldehyde.

10. The method of claim 1 wherein said implant body consists essentially of collagen.

11. The method of claim 1 wherein said implant body has a length and a width and said implant body comprises a central cavity running the length of the implant.

12. The method of claim 1 wherein said implant body has a textured outer surface.

13. The method of claim 1 wherein said implant body has a tapered shape.

* * * * *